(12) United States Patent  (10) Patent No.: US 7,968,851 B2
Rousso et al.  (45) Date of Patent: Jun. 28, 2011

(54) DYNAMIC SPECT CAMERA

(75) Inventors: Benny Rousso, Rishon-LeZion (IL); Omer Ziv, Rechovot (IL); Michael Nagler, Tel-Aviv (IL); Shlomo Ben-Haim, London (GB)

(73) Assignee: Spectrum Dynamics LLC, Orangeburg, NY (US)

( * ) Notice: Subject to any disclaimer, the term of this patent is extended or adjusted under 35 U.S.C. 154(b) by 0 days.

(21) Appl. No.: 12/728,383

(22) Filed: Mar. 22, 2010

(65) Prior Publication Data

US 2010/0245354 A1  Sep. 30, 2010

Related U.S. Application Data

(63) Continuation of application No. 12/084,559, filed as application No. PCT/IL2006/001291 on Nov. 9, 2006, now Pat. No. 7,705,316, which is a continuation-in-part of application No. PCT/IL2006/000840, filed on Jul. 19, 2006, and a continuation-in-part of application No. PCT/IL2006/000834, filed on Jul. 19, 2006, and a continuation-in-part of application No. PCT/IL2006/000562, filed on May 11, 2006, and a continuation-in-part of application No. PCT/IL2006/000059, filed on Jan. 15, 2006, and a continuation-in-part of application No.

(Continued)

(30) Foreign Application Priority Data

Oct. 10, 2005 (IL) .......................................... 171346
Nov. 27, 2005 (IL) .......................................... 172349

(51) Int. Cl.
  *H01L 27/146* (2006.01)
(52) U.S. Cl. ............................................. 250/370.09
(58) Field of Classification Search ................ 387/98.8; 250/370.01–370.15; 382/289, 294
  See application file for complete search history.

(56) References Cited

U.S. PATENT DOCUMENTS 2,776,377 A  1/1957 Anger
(Continued)

FOREIGN PATENT DOCUMENTS

DE  1516429  12/1969
(Continued)

OTHER PUBLICATIONS

Pluim et al., "Image registration by maximization of combined mutual information and gradient information," 2000, IEEE Transactions on Medical Imaging, vol. 10, No. 8, pp. 1-6.*

(Continued)

*Primary Examiner* — David P Porta
*Assistant Examiner* — Kiho Kim

(57) ABSTRACT

A method of reconstruction of a radioactive emission image. The method comprises providing a first system of voxels for a region of interest, obtaining radioactive-emission data from the region of interest, performing a first reconstruction, based on the radioactive-emission data and the first system of voxels, to obtain a first image, correcting the first system of voxels, by aligning voxel boundaries with object boundaries, based on the first image; thus obtaining a second system of voxels, and performing a second reconstruction, based on the radioactive-emission data and the second system of voxels, thus obtaining a second image.

19 Claims, 25 Drawing Sheets
(17 of 25 Drawing Sheet(s) Filed in Color)

Related U.S. Application Data

(63) PCT/IL2005/001215, filed on Nov. 16, 2005, and a continuation-in-part of application No. PCT/IL2005/001173, filed on Nov. 9, 2005, and a continuation-in-part of application No. PCT/IL2005/000575, filed on Jun. 1, 2005, and a continuation-in-part of application No. PCT/IL2005/000572, filed on Jun. 1, 2005, and a continuation-in-part of application No. PCT/IL2005/000048, filed on Jan. 13, 2005, said application No. 12/084,559 is a continuation-in-part of application No. 11/034,007, filed on Jan. 13, 2005, now Pat. No. 7,176,466.

(60) Provisional application No. 60/816,970, filed on Jun. 28, 2006, provisional application No. 60/800,846, filed on May 17, 2006, provisional application No. 60/800,845, filed on May 17, 2006, provisional application No. 60/799,688, filed on May 11, 2006, provisional application No. 60/763,458, filed on Jan. 31, 2006, provisional application No. 60/754,199, filed on Dec. 28, 2005, provisional application No. 60/750,597, filed on Dec. 15, 2005, provisional application No. 60/750,334, filed on Dec. 15, 2005, provisional application No. 60/750,287, filed on Dec. 13, 2005, provisional application No. 60/741,440, filed on Dec. 2, 2005, provisional application No. 60/720,652, filed on Sep. 27, 2005, provisional application No. 60/720,541, filed on Sep. 27, 2005, provisional application No. 60/720,034, filed on Sep. 26, 2005, provisional application No. 60/702,979, filed on Jul. 28, 2005, provisional application No. 60/700,753, filed on Jul. 20, 2005, provisional application No. 60/700,752, filed on Jul. 20, 2005, provisional application No. 60/700,318, filed on Jul. 19, 2005, provisional application No. 60/700,317, filed on Jul. 19, 2005, provisional application No. 60/700,299, filed on Jul. 19, 2005, provisional application No. 60/691,780, filed on Jun. 20, 2005, provisional application No. 60/675,892, filed on Apr. 29, 2005, provisional application No. 60/648,690, filed on Feb. 2, 2005, provisional application No. 60/648,385, filed on Feb. 1, 2005, provisional application No. 60/640,215, filed on Jan. 3, 2005, provisional application No. 60/636,088, filed on Dec. 16, 2004, provisional application No. 60/635,630, filed on Dec. 14, 2004, provisional application No. 60/632,515, filed on Dec. 3, 2004, provisional application No. 60/632,236, filed on Dec. 2, 2004, provisional application No. 60/630,561, filed on Nov. 26, 2004, provisional application No. 60/628,105, filed on Nov. 17, 2004, provisional application No. 60/625,971, filed on Nov. 9, 2004, provisional application No. 60/575,369, filed on Jun. 1, 2004, provisional application No. 60/535,830, filed on Jan. 13, 2004.

U.S. PATENT DOCUMENTS

| Patent No. | Date | Inventor |
|---|---|---|
| 3,340,866 A | 9/1967 | Nöller |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 4,015,592 A | 4/1977 | Bradley-Moore |
| 4,278,077 A | 7/1981 | Mizumoto |
| 4,364,377 A | 12/1982 | Smith |
| 4,521,688 A | 6/1985 | Yin |
| H12 H | 1/1986 | Bennett et al. |
| 4,595,014 A | 6/1986 | Barrett et al. |
| 4,674,107 A | 6/1987 | Urban et al. |
| 4,689,041 A | 8/1987 | Corday et al. |
| 4,689,621 A | 8/1987 | Kleinberg |
| 4,773,430 A | 9/1988 | Porath |
| 4,828,841 A | 5/1989 | Porter et al. |
| 4,844,067 A | 7/1989 | Ikada et al. |
| 4,844,076 A | 7/1989 | Lesho et al. |
| 4,893,013 A | 1/1990 | Denen et al. |
| 4,928,250 A | 5/1990 | Greenberg et al. |
| 4,929,832 A | 5/1990 | Ledley |
| 4,951,653 A | 8/1990 | Fry et al. |
| 4,959,547 A | 9/1990 | Carroll et al. |
| 4,995,396 A | 2/1991 | Inaba et al. |
| 5,014,708 A | 5/1991 | Hayashi et al. |
| 5,032,729 A | 7/1991 | Charpak |
| 5,033,998 A | 7/1991 | Corday et al. |
| 5,070,878 A | 12/1991 | Denen |
| 5,088,492 A | 2/1992 | Takayama et al. |
| 5,119,818 A | 6/1992 | Carroll et al. |
| 5,151,598 A | 9/1992 | Denen |
| 5,170,055 A | 12/1992 | Carroll et al. |
| 5,170,789 A | 12/1992 | Narayan et al. |
| 5,243,988 A | 9/1993 | Sieben et al. |
| 5,246,005 A | 9/1993 | Carroll et al. |
| 5,249,124 A | 9/1993 | DeVito |
| 5,279,607 A | 1/1994 | Schentag et al. |
| 5,299,253 A | 3/1994 | Wessels |
| 5,307,808 A | 5/1994 | Dumoulin et al. |
| 5,383,456 A | 1/1995 | Arnold et al. |
| 5,386,446 A | 1/1995 | Fujimoto et al. |
| 5,395,366 A | 3/1995 | D'Andrea |
| 5,399,868 A | 3/1995 | Jones et al. |
| 5,415,181 A | 5/1995 | Hogrefe et al. |
| 5,441,050 A | 8/1995 | Thurston et al. |
| 5,448,073 A | 9/1995 | Jeanguillaume |
| 5,475,219 A | 12/1995 | Olson |
| 5,484,384 A | 1/1996 | Fearnot |
| 5,489,782 A | 2/1996 | Wernikoff |
| 5,493,595 A | 2/1996 | Schoolman |
| 5,519,221 A | 5/1996 | Weinberg |
| 5,572,999 A | 11/1996 | Funda et al. |
| 5,579,766 A | 12/1996 | Gray |
| 5,604,531 A | 2/1997 | Iddan et al. |
| 5,617,858 A | 4/1997 | Taverna et al. |
| 5,635,717 A | 6/1997 | Popescu |
| 5,657,759 A | 8/1997 | Essen-Moller |
| 5,672,877 A | 9/1997 | Liebig et al. |
| 5,682,888 A | 11/1997 | Olson et al. |
| 5,690,691 A | 11/1997 | Chen et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,744,805 A | 4/1998 | Raylman et al. |
| 5,803,914 A | 9/1998 | Ryals et al. |
| 5,811,814 A | 9/1998 | Leone et al. |
| 5,821,541 A | 10/1998 | Tumer |
| 5,833,603 A | 11/1998 | Kovacs et al. |
| 5,842,977 A | 12/1998 | Lesho et al. |
| 5,846,513 A | 12/1998 | Carroll et al. |
| 5,857,463 A | 1/1999 | Thurston et al. |
| 5,871,013 A | 2/1999 | Wainer et al. |
| 5,880,475 A | 3/1999 | Oka et al. |
| 5,891,030 A | 4/1999 | Johnson et al. |
| 5,900,533 A | 5/1999 | Chou |
| 5,916,167 A | 6/1999 | Kramer et al. |
| 5,928,150 A | 7/1999 | Call |
| 5,932,879 A | 8/1999 | Raylman et al. |
| 5,939,724 A | 8/1999 | Eisen et al. |
| 5,961,457 A | 10/1999 | Raylman et al. |
| 5,984,860 A | 11/1999 | Shan |
| 5,987,350 A | 11/1999 | Thurston |
| 5,993,378 A | 11/1999 | Lemelson |
| 6,002,480 A | 12/1999 | Izatt et al. |

| | | | |
|---|---|---|---|
| 6,072,177 A | 6/2000 | McCroskey et al. | |
| 6,076,009 A | 6/2000 | Raylman et al. | |
| 6,082,366 A | 7/2000 | Andra et al. | |
| 6,107,102 A | 8/2000 | Ferrari | |
| 6,115,635 A | 9/2000 | Bourgeois | |
| 6,129,670 A | 10/2000 | Burdette et al. | |
| 6,132,372 A | 10/2000 | Essen-Moller | |
| 6,135,955 A | 10/2000 | Madden et al. | |
| 6,173,201 B1 | 1/2001 | Front | |
| 6,205,347 B1 | 3/2001 | Morgan et al. | |
| 6,212,423 B1 | 4/2001 | Krakovitz | |
| 6,236,878 B1 | 5/2001 | Taylor et al. | |
| 6,236,880 B1 | 5/2001 | Raylman et al. | |
| 6,239,438 B1 | 5/2001 | Schubert | |
| 6,240,312 B1 | 5/2001 | Alfano et al. | |
| 6,242,743 B1 | 6/2001 | DeVito et al. | |
| 6,246,901 B1 | 6/2001 | Benaron | |
| 6,261,562 B1 | 7/2001 | Xu et al. | |
| 6,263,229 B1 | 7/2001 | Atalar et al. | |
| 6,271,524 B1 | 8/2001 | Wainer et al. | |
| 6,271,525 B1 | 8/2001 | Majewski et al. | |
| 6,280,704 B1 | 8/2001 | Schutt et al. | |
| 6,310,968 B1 | 10/2001 | Hawkins et al. | |
| 6,324,418 B1 | 11/2001 | Crowley et al. | |
| 6,339,652 B1 | 1/2002 | Hawkins et al. | |
| 6,346,706 B1 | 2/2002 | Rogers et al. | |
| 6,368,331 B1 | 4/2002 | Front et al. | |
| 6,381,349 B1 | 4/2002 | Zeng et al. | |
| 6,392,235 B1 | 5/2002 | Barrett et al. | |
| 6,407,391 B1 | 6/2002 | Mastrippolito et al. | |
| 6,415,046 B1 | 7/2002 | Kerut, Sr. | |
| 6,420,711 B2 | 7/2002 | Tuemer | |
| 6,426,917 B1 | 7/2002 | Tabanou et al. | |
| 6,429,431 B1 | 8/2002 | Wilk | |
| 6,431,175 B1 | 8/2002 | Penner et al. | |
| 6,453,199 B1 | 9/2002 | Kobozev | |
| 6,484,051 B1 | 11/2002 | Daniel | |
| 6,490,476 B1 | 12/2002 | Townsend et al. | |
| 6,510,336 B1 | 1/2003 | Daghighian et al. | |
| 6,516,213 B1 | 2/2003 | Nevo | |
| 6,525,320 B1 | 2/2003 | Juni | |
| 6,525,321 B2 | 2/2003 | Juni | |
| 6,549,646 B1 | 4/2003 | Yeh et al. | |
| 6,560,354 B1 | 5/2003 | Maurer et al. | |
| 6,567,687 B2 | 5/2003 | Front et al. | |
| 6,584,348 B2 | 6/2003 | Glukhovsky | |
| 6,587,710 B1 | 7/2003 | Wainer | |
| 6,592,520 B1 | 7/2003 | Peszynski et al. | |
| 6,602,488 B1 | 8/2003 | Daghighian | |
| 6,607,301 B1 | 8/2003 | Glukhovsky et al. | |
| 6,611,141 B1 | 8/2003 | Schulz et al. | |
| 6,614,453 B1 | 9/2003 | Suri et al. | |
| 6,628,983 B1 | 9/2003 | Gagnon | |
| 6,628,984 B2 | 9/2003 | Weinberg | |
| 6,632,216 B2 | 10/2003 | Houzego et al. | |
| 6,633,658 B1 | 10/2003 | Dabney et al. | |
| 6,638,752 B2 | 10/2003 | Contag et al. | |
| 6,643,538 B1 | 11/2003 | Majewski et al. | |
| 6,662,036 B2 | 12/2003 | Cosman | |
| 6,680,750 B1 | 1/2004 | Tournier et al. | |
| 6,697,660 B1 | 2/2004 | Robinson | |
| 6,748,259 B1 | 6/2004 | Benaron et al. | |
| 6,771,802 B1 | 8/2004 | Patt et al. | |
| 6,943,355 B2 | 9/2005 | Shwartz et al. | |
| 6,963,770 B2 | 11/2005 | Scarantino et al. | |
| 7,043,063 B1 | 5/2006 | Noble et al. | |
| 7,142,634 B2 | 11/2006 | Engler et al. | |
| 7,176,466 B2 | 2/2007 | Rousso et al. | |
| 7,187,790 B2 | 3/2007 | Sabol et al. | |
| 7,468,513 B2 | 12/2008 | Charron et al. | |
| 7,490,085 B2 | 2/2009 | Walker et al. | |
| 2002/0072784 A1 | 6/2002 | Sheppard, Jr. et al. | |
| 2002/0085748 A1 | 7/2002 | Baumberg | |
| 2002/0087101 A1 | 7/2002 | Barrick et al. | |
| 2002/0099295 A1 | 7/2002 | Gil et al. | |
| 2002/0103431 A1 | 8/2002 | Toker et al. | |
| 2002/0168317 A1 | 11/2002 | Daighighian et al. | |
| 2002/0183645 A1 | 12/2002 | Nachaliel | |
| 2002/0188197 A1 | 12/2002 | Bishop et al. | |
| 2003/0001837 A1 | 1/2003 | Baumberg | |
| 2003/0013966 A1 | 1/2003 | Barnes et al. | |
| 2003/0063787 A1 | 4/2003 | Natanzon et al. | |
| 2003/0081716 A1 | 5/2003 | Tumer | |
| 2003/0191430 A1 | 10/2003 | D'Andrea et al. | |
| 2003/0202629 A1 | 10/2003 | Dunham et al. | |
| 2003/0208117 A1 | 11/2003 | Shwartz et al. | |
| 2003/0216631 A1 * | 11/2003 | Bloch et al. | 600/407 |
| 2004/0003001 A1 | 1/2004 | Shimura | |
| 2004/0010397 A1 | 1/2004 | Barbour et al. | |
| 2004/0015075 A1 | 1/2004 | Kimchy et al. | |
| 2004/0054248 A1 | 3/2004 | Kimchy et al. | |
| 2004/0054278 A1 | 3/2004 | Kimchy et al. | |
| 2004/0081623 A1 | 4/2004 | Eriksen et al. | |
| 2004/0086437 A1 | 5/2004 | Jackson et al. | |
| 2004/0101176 A1 | 5/2004 | Mendonca et al. | |
| 2004/0116807 A1 | 6/2004 | Amrami et al. | |
| 2004/0153128 A1 | 8/2004 | Suresh et al. | |
| 2004/0171924 A1 | 9/2004 | Mire et al. | |
| 2004/0204646 A1 | 10/2004 | Nagler et al. | |
| 2004/0251419 A1 | 12/2004 | Nelson et al. | |
| 2005/0020915 A1 | 1/2005 | Belardinelli et al. | |
| 2005/0055174 A1 | 3/2005 | David et al. | |
| 2005/0205792 A1 | 9/2005 | Rousso et al. | |
| 2005/0211909 A1 | 9/2005 | Smith | |
| 2005/0215889 A1 | 9/2005 | Patterson, II | |
| 2005/0253073 A1 | 11/2005 | Joram et al. | |
| 2005/0266074 A1 | 12/2005 | Zilberstein et al. | |
| 2006/0074290 A1 * | 4/2006 | Chen et al. | 600/407 |
| 2006/0160157 A1 | 7/2006 | Zuckerman | |
| 2006/0237652 A1 | 10/2006 | Kimchy et al. | |
| 2007/0156047 A1 | 7/2007 | Nagler et al. | |
| 2007/0166227 A1 | 7/2007 | Liu et al. | |
| 2007/0194241 A1 | 8/2007 | Rousso et al. | |
| 2008/0033291 A1 | 2/2008 | Rousso et al. | |
| 2008/0042067 A1 | 2/2008 | Rousso et al. | |
| 2008/0128626 A1 | 6/2008 | Rousso et al. | |
| 2008/0230705 A1 | 9/2008 | Rousso et al. | |
| 2008/0237482 A1 | 10/2008 | Shahar et al. | |
| 2008/0260228 A1 | 10/2008 | Dichterman et al. | |
| 2008/0260637 A1 | 10/2008 | Dickman | |
| 2008/0277591 A1 | 11/2008 | Shahar et al. | |
| 2009/0078875 A1 | 3/2009 | Rousso et al. | |
| 2009/0190807 A1 | 7/2009 | Rousso et al. | |

FOREIGN PATENT DOCUMENTS

| | | |
|---|---|---|
| DE | 19814199 | 10/1999 |
| DE | 19815362 | 10/1999 |
| EP | 0543626 | 5/1993 |
| EP | 0697193 | 2/1996 |
| EP | 0887661 | 12/1998 |
| GB | 2031142 | 4/1980 |
| JP | 06-109848 | 4/1994 |
| WO | WO 92/00402 | 1/1992 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/31522 | 6/2000 |
| WO | WO 01/89384 | 11/2001 |
| WO | WO 02/16965 | 2/2002 |
| WO | WO 02/058531 | 8/2002 |
| WO | WO 2004/042546 | 5/2004 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/075333 | 7/2006 |
| WO | WO 2007/010534 | 1/2007 |
| WO | WO 2007/010537 | 1/2007 |
| WO | WO 2007/074467 | 7/2007 |
| WO | WO 2008/010227 | 1/2008 |
| WO | WO 2008/075362 | 6/2008 |

OTHER PUBLICATIONS

Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Communication Pursuant to Article 94(3) EPC Dated Oct. 21, 2009 From the European Patent Office Re.: Application No. 02716285.8.
Communication Pursuant to Article 94(3) EPC Dated Jul. 22, 2009 From the European Patent Office Re.: Application No. 06809851.6.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Jul. 11, 2008 From the International Searching Authority of the Patent Cooperation Treaty Re.: Application No. PCT/IL06/01511.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re.: Application No. PCT/IL07/00918.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Sep. 17, 2009 From the US Patent and Trademark Office Re.: U.S. Appl. No. 10/533,568. Suppl. IDS VIII in 25855.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated May 3, 2007 From the US Patent and Trademark Office Re.: U.S. Appl. No. 10/240,239.

Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated Oct. 7, 2008 From the US Patent and Trademark Office Re.: U.S. Appl. No. 10/616,301.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Aug. 10, 2007 From the US Patent and Trademark Office Re.: U.S. Appl. No. 10/836,223.
Official Action Dated Aug. 11, 2009 From the US Patent and Trademark Office Re.: U.S. Appl. No. 09/641,973.
Official Action Dated Mar. 11, 2010 From the US Patent and Trademark Office Re.: U.S. Appl. No. 11/607,075.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Jul. 15, 2009 From the US Patent and Trademark Office Re.: U.S. Appl. No. 10/616,301.
Official Action Dated Mar. 15, 2004 From the US Patent and Trademark Office Re.: U.S. Appl. No. 09/725,316.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Sep. 16, 2009 From the US Patent and Trademark Office Re.: U.S. Appl. No. 09/727,464.
Official Action Dated Jan. 17, 2006 From the United States Patent and Trademark Office Re.: U.S. Appl. No. 11/034,007.
Official Action Dated Mar. 19, 2010 From the US Patent and Trademark Office Re.: U.S. Appl. No. 10/240,239.
Official Action Dated Apr. 20, 2006 From the United States Patent and Trademark Office Re.: U.S. Appl. No. 10/240,239.
Official Action Dated Jul. 20, 2009 From the US Patent and Trademark Office Re.: U.S. Appl. No. 11/980,617.
Official Action Dated Mar. 21, 2008 From the US Patent and Trademark Office Re.: U.S. Appl. No. 10/533,568.
Official Action Dated Sep. 21, 2009 From the US Patent and Trademark Office Re.: U.S. Appl. No. 11/798,017.
Official Action Dated Dec. 23, 2008 From the US Patent and Trademark Office Re.: U.S. Appl. No. 09/727,464.
Official Action Dated Feb. 23, 2010 From the US Patent and Trademark Office Re.: U.S. Appl. No. 09/641,973.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Nov. 26, 2008 From the US Patent and Trademark Office Re.: U.S. Appl. No. 10/240,239.
Official Action Dated Aug. 28, 2009 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Official Action Dated Oct. 30, 2009 From the US Patent and Trademark Office Re.: U.S. Appl. No. 11/980,690.
Official Action Dated Sep. 30, 2008 From the US Patent and Trademark Office Re.: U.S. Appl. No. 10/616,301.
Response Dated Apr. 7, 2009 to Official Action of Oct. 7, 2008 From the US Patent and Trademark Office Re.: U.S. Appl. No. 10/616,301.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Oct. 14, 2009 to Official Action of May 14, 2009 From the US Patent and Trademark Office Re.: U.S. Appl. No. 11/656,548.
Response Dated Mar. 15, 2007 to Official Action of Dec. 15, 2006 From the US Patent and Trademark Office Re.: U.S. Appl. No. 10/616,301.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Sep. 22, 2008 to Official Action of Jun. 25, 2008 From the US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Response Dated Oct. 31, 2007 to Official Action of Jul. 12, 2007 From the US Patent and Trademark Office Re.: U.S. Appl. No. 10/616,301.
Response to the International Search Report and the Written Opinion of Oct. 10, 2006 From the International Searching Authority Re.: Application No. PCT/IL06/00059.
Second International Search Report Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.

Supplementary Partial European Search Report and the European Search Opinion Dated Oct. 16, 2009 From the European Patent Office Re.: Application No. 06756259.5.

Supplementary Partial European Search Report Dated Sep. 4, 2007 From the European Patent Office Re.: Application No. 0 2716285.8.

Supplementary Partial European Search Report Dated Nov. 11, 2008 From the European Patent Office Re.: Application No. 01951883.6.

Supplementary Partial European Search Report Dated Nov. 20, 2007 From the European Patent Office Re.: Application No. 02716285.8.

Translation of Office Action Dated May 13, 2005 From the Patent Office of the People's Republic of China Re.: Application No. 01817689.5.

Written Opinion Dated Feb. 1, 2006 From the International Searching Authority of the Patent Cooperation Treaty Re.: Application No. PCT/IL05/00048.

Written Opinion Dated Jul. 1, 2008 From the International Searching Authority of the Patent Cooperation Treaty Re.: Application No. PCT/IL06/00834.

Written Opinion Dated Jul. 2, 2007 From the International Searching Authority of the Patent Cooperation Treaty Re.: Application No. PCT/IL2006/001291.

Written Opinion Dated Oct. 10, 2006 From the International Searching Authority of the Patent Cooperation Treaty Re.: Application No. PCT/IL06/00059.

Written Opinion Dated Oct. 15, 2008 From the International Searching Authority Re.: Application No. PCT/IL07/00918.

Written Opinion Dated Mar. 23, 2006 From the International Searching Authority of the Patent Cooperation Treaty Re.: Application No. PCT/IL05/00572.

Written Opinion Dated May 24, 2007 From the International Searching Authority of the Patent Cooperation Treaty Re.: Application No. PCT/IL05/00575.

Written Opinion Dated Jul. 25, 2008 From the International Searching Authority of the Patent Cooperation Treaty Re.: Application No. PCT/IL05/001173.

Written Opinion Dated Mar. 26, 2007 From the International Searching Authority of the Patent Cooperation Treaty Re.: Application No. PCT/IL05/00394.

Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.

Bloch et al. "Application of Computerized Tomography to Radiation Therapy and Surgical Planning", Proceedings of the IEEE, 71(3): 351-355, Mar. 1983.

Bromiley et al. "Attenuation Correction in PET Using Consistency Conditions and A Three-Dimensional Template", IEEE Transactions on Nuclear Science, XP002352920, 48(4): 1371-1377, 2001. p. 1376, col. 2, § 2.

Corstens et al. "Nuclear Medicine's Role in Infection and Inflammation", The Lancet, 354: 765-770, 1999.

Day et al. "Localization of Radioiodinated Rat Fibrogen in Transplanted Rat Tumors", Journal of the National Cancer Institute, 23(4): 799-812, 1959.

Erbil et al. "Use and Limitations of Serum Total and Lipid-Bound Sialic Acid Concentrations as Markers for Colorectal Cancer", Cancer, 55: 404-409, 1985.

Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.

Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.

Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.

Gugnin et al "Radiocapsule for Recording The Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).

Hassan et al. "A Radiotelemetry Pill for the Measurement of Ionising Radiation Using A Mercuric Iodide Detector", Physics in Medicine and Biology, 23(2): 302-308, 1978.

Hayakawa et al. "A PET-MRI Registration Technique for PET Studies of the Rat Brain", Nuclear Medicine & Biology, 27: 121-125, 2000. p. 121, col. 1.

Hoffman et al. "Intraoperative Probes and Imaging Probes", European Journal of Nuclear Medicine, 26(8): 913-935, 1999.

Huesman et al. "Kinetic Parameter Estimation From SPECT Cone-Beam Projection Measurements", Physics in Medicine and Biology, 43(4): 973-982, 1998.

Jeanguillaume et al. "From the Whole-Body Counting to Imaging: The Computer Aided Collimation Gamma Camera Project (CACAO)", Radiation Projection Dosimetry 89(3-4): 349-352, 2000.

Jessup "Tumor Markers—Prognostic and Therapeutic Implications for Colorectal Carcinoma", Surgical Oncology, 7: 139-151, 1998.

Kadrmas et al. "Static Versus Dynamic Teboroxime Myocardial Perfusion SPECT in Canines", IEEE Transactions on Nuclear Science, 47(3): 1112-1117, Jun. 2000.

Kinahan et al. "Attenuation Correction for A Combined 3D PET/CT Scanner", Medical Physics, 25(10): 2046-2053, Oct. 1998.

Kojima et al. "Quantitative Planar Imaging Method for Measurement of Renal Activity by Using A Conjugate-Emission Image and Transmission Data", Medical Physics, 27(3): 608-615, 2000. p. 608.

Lavallée et al. "Building A Hybrid Patient's Model for Augmented Reality in Surgery: A Registration Problem", Computing in Biological Medicine, 25(2): 149-164, 1995.

Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, p. 1137, First col., 2nd §.

Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.

Moil et al. "Overexpression of Matrix Metalloproteinase-7mRNA in Human Colon Carcinomas", Cancer, 75: 1516-1519, 1995.

Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.

Piperno et al. "Breast Cancer Screening by Impedance Measurements", Frontiers Med. Biol. Engng., 2(2): 11-17, 1990.

Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.

Quartuccia et al. "Computer Assisted Collimation Gama Camera: A New Approach to Imaging Contaminated Tissues", Radiation Projection Dosimetry, 89(3-4): 343-348, 2000.

Rajshekhar "Continuous Impedence Monitoring During CT-Guided Stereotactic Surgery: Relative Value in Cystic and Solid Lesions", British Journal of Neurosurgery, 6: 439-444, 1992.

Reutter et al. "Direct Least Squares Estimation of Spatiotemporal Distributions From Dynamic SPECT Projections Using A Spatial Segmentation and Temporal B-Splines", IEEE Transactions on Medical Imaging, 19(5): 434-450, 2000.

Reutter et al. "Kinetic Parameter Estimation From Attenuated SPECT Projection Measurements", IEEE Transactions on Nuclear Science, 45(6): 3007-3013, 1998.

Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.

Takahashi et al. "Attenuation Correction of Myocardial Spect Images With X-Ray CT: Effects of Registration Errors Between X-Ray CT and SPECT", Annals of Nuclear Medicine, 16(6): 431-435, Sep. 2002.

Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.

Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.

Zaidi et al. "Magenetic Resonance Imaging-Guided Attenuation and Scatter Corrections in Three-Dimensional Brain Positron Emission Tomography", Medical Physics, 30(5): 937-948, May 2003.

Zaidi et al. "MRI-Guided Attenuation Correction in 3D Brain PET", Neuroimage Human Brain Mapping 2002 Meeting, 16(2): Abstract 504, Jun. 2002.

Zhang et al. "An Innovative High Efficiency and High Resolution Probe for Prostate Imaging", The Journal of Nuclear Medicine, 68: 18, 2000. Abstract.

Official Action Dated Apr. 9, 2010 From the US Patent and Trademark Office Re.: U.S. Appl. No. 11/798,017.

Communication Pursuant to Article 93(3) EPC Dated Mar. 8, 2010 From the European Patent Office Re.: Application No. 06832278.3.

International Search Report Dated Oct. 10, 2006 From the International Searching Authority of the Patent Cooperation Treaty Re.: Application No. PCT/IL06/00059.

Written Opinion Dated Aug. 3, 2006 From the International Searching Authority of the Patent Cooperation Treaty Re.: Application No. PCT/IL05/001173.

Response Dated May 11, 2010 to Official Action of Mar. 11, 2010 From the US Patent and Trademark Office Re.: U.S. Appl. No. 11/607,075.

Response Dated May 26, 2010 to Official Action of Mar. 19, 2010 From the US Patent and Trademark Office Re.: U.S. Appl. No. 10/240,239.

Communication Pursuant to Article 94(3) EPC Dated Apr. 16, 2010 From the European Patent Office Re. Application No. 01951883.6.

Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.

Response Dated Jul. 1, 2010 to Official Action of Mar. 2, 2010 From the US Patent and Trademark Office Re.: U.S. Appl. No. 11/980,617.

Response Dated Jun. 1, 2010 to Official Action of Mar. 1, 2010 From the US Patent and Trademark Office Re.: U.S. Appl. No. 11/794,799.

Response Dated Jul. 8, 2010 to Communication Pursuant to Article 94(3) EPC of Mar. 8, 2010 From the European Patent Office Re.: Application No. 06832278.3.

Official Action Dated Jul. 19, 2010 From the US Patent and Trademark Office Re.: U.S. Appl. No. 11/607,075.

Official Action Dated Jul. 19, 2010 From the US Patent and Trademark Office Re.: U.S. Appl. No. 11/656,548.

Response Dated Jul. 1, 2010 to Official Action of Mar. 2, 2010 From the US Patent and Trademark Office Re.: U.S. Appl. No. 10/836,223.

Response Dated Jul. 8, 2010 to Official Action of Apr. 9, 2010 From the US Patent and Trademark Office Re.: U.S. Appl. No. 11/798,017.

Response Dated Jun. 23, 2010 to Official Action of Feb. 23, 2010 From the US Patent and Trademark Office Re.: U.S. Appl. No. 09/641,973.

Official Action Dated Jul. 27, 2010 From the US Patent and Trademark Office Re.: U.S. Appl. No. 10/616,307.

Response Dated Jul. 26, 2010 to Official Action of Apr. 28, 2010 From the US Patent and Trademark Office Re.: U.S. Appl. No. 10/616,301.

Notice of Allowance Dated Jun. 30, 2010 From the United States Patent and Trademark Office Re.: U.S. Appl. No. 09/727,464.

Official Action Dated Aug. 3, 2010 From the US Patent and Trademark Office Re.: U.S. Appl. No. 11/980,690.

Supplemental Response After Interview Dated Aug. 4, 2010 to Official Action of Mar. 2, 2010 From the US Patent and Trademark Office Re.: U.S. Appl. No. 11/980,617.

Notice of Allowance Dated Jul. 22, 2010 From the US Patent and Trademark Office Re.: U.S. Appl. No. 11/794,799.

Response Dated Aug. 16, 2010 to Communication Pursuant to Article 94(3) EPC of Apr. 16, 2010 From the European Patent Office Re. Application No. 01951883.6.

Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.

Response Dated Aug. 25, 2010 to Official Action of Jul. 27, 2010 From the US Patent and Trademark Office Re.: U.S. Appl. No. 10/616,307.

Communication Pursuant to Article 94(3) EPC Dated May 12, 2010 From the European Patent Office Re.: Application No. 06809851.6.

Notice of Allowance Dated Aug. 25, 2010 From the US Patent and Trademark Office Re. U.S. Appl. No. 11/980,617.

Response Dated Sep. 8, 2010 to Communication Pursuant to Article 94(3) EPC Dated May 12, 2010 From the European Patent Office Re.: Application No. 06809851.6.

Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.

Official Action Dated Dec. 8, 2010 From the US Patent and Trademark Office Re.: U.S. Appl. No. 11/980,690.

Official Action Dated Nov. 10, 2010 From the US Patent and Trademark Office Re.: U.S. Appl. No. 10/616,307.

Official Action Dated Nov. 10, 2010 From the US Patent and Trademark Office Re.: U.S. Appl. No. 10/836,223.

Official Action Dated Nov. 23, 2010 From the US Patent and Trademark Office Re.: U.S. Appl. No. 11/656,548.

Response Dated Nov. 18, 2010 to Official Action of Jul. 19, 2010 From the US Patent and Trademark Office Re.: U.S. Appl. No. 11/607,075.

Notice of Allowance Dated Dec. 17, 2010 From the US Patent and Trademark Office Re. U.S. Appl. No. 11/980,617.

Official Action Dated Dec. 8, 2010 From the US Patent and Trademark Office Re.: U.S. Appl. No. 09/641,973.

Official Action Dated Dec. 28, 2010 From the US Patent and Trademark Office Re.: U.S. Appl. No. 11/607,075.

Response Dated Dec. 15, 2010 to Official Action of Jul. 19, 2010 From the US Patent and Trademark Office Re.: U.S. Appl. No. 11/656,548.

Response dated Sep. 1, 2010 to Official Action of Aug. 3, 2010 From the US Patent and Trademark Office Re.: U.S. Appl. No. 11/980,690.

Official Action Dated Sep. 30, 2010 From the US Patent and Trademark Office Re.: U.S. Appl. No. 11/798,017.

Response Dated Oct. 5, 2010 to Official Action of Jul. 19, 2010 From the US Patent and Trademark Office Re.: U.S. Appl. No. 11/656,548.

Beekman et al. "Efficient Fully 3-D Iterative SPECT Reconstruction With Monte Carlo-Based Scatter Compensation", IEEE Transactions on Medical Imaging, 21(8): 867-877, Aug. 2002.

Brown et al. "Method for Segmenting Chest CT Image Data Using An Anatomical Model: Preliminary Results", IEEE Transactions on Medical Imaging, 16(6): 828-839, Dec. 1997.

Del Guerra et al. "An Integrated PET-SPECT Small Animal Imager: Preliminary Results", Nuclear Science Symposium, IEEE Records, 1: 541-544, 1999.

Official Action Dated Mar. 15, 2004 From the US Patent and Trademark Office Re.: U.S. Appl. No. 09/765,316.

Official Action Dated Jan. 31, 2011 From the US Patent and Trademark Office Re. U.S. Appl. No. 11/667,793.

Official Action Dated Jan. 28, 2011 From the US Patent and Trademark Office Re.: U.S. Appl. No. 09/641,973.

Response Dated Feb. 10, 2011 to Official Action of Nov. 10, 2010 From the US Patent and Trademark Office Re.: U.S. Appl. No. 10/616,307.

Response Dated Jan. 31, 2011 to Official Action of Sep. 30, 2010 From the US Patent and Trademark Office Re.: U.S. Appl. No. 11/798,017.

Response dated Jan. 27, 2011 to official action of Nov. 1, 2010 from the US patent and trademark office re.: U.S. Appl. No. 11/980,690.

Interview Summary Dated Mar. 25, 2011 From the US Patent and Trademark Office Re.: U.S. Appl. No. 10/836,223.

Response Dated Mar. 3, 2011 to Notice of Non-Compliant Amendment of Feb. 14, 2011 From the US Patent and Trademark Office Re.: U.S. Appl. No. 10/616,307.

Response Dated Apr. 5, 2011 to Official Action of Nov. 10, 2010 From the US Patent and Trademark Office Re.: U.S. Appl. No. 10/836,223.

Response Dated Mar. 8, 2011 to Official Action of Dec. 8, 2010 From the US Patent and Trademark Office Re.: U.S. Appl. No. 11/980,690.

Supplementary European Search Report and the European Search Opinion Dated Mar. 16, 2011 From the European Patent Office Re. Application No. 05803689.8.

Herrmann et al., "Mitochondrial Proteome: Altered Cytochtrome C Oxidase Subunit Levels in Prostate Cancer", Proteomics, XP002625778, 3(9): 1801-1810, Sep. 2003.

Krieg et al., "Mitochondrial Proteome: Cancer-Altered Metabolism Associated With Cytochrome C Oxidase Subunit Level Variation", Proteomics, XP002625779, 4(9): 2789-2795, Sep. 2004.

Mao et al., "Human Prostatic Carcinoma: An Electron Microscope Study", Cancer Research, XP002625777, 26(5): 955-973, May 1966.

Storey et al., "Tc-99m Sestamibi Uptake in Metastatic Prostate Carcinoma", Clinical Nuclear Medicine, XP009145398, 25(2): 133-134, Feb. 2000.

* cited by examiner

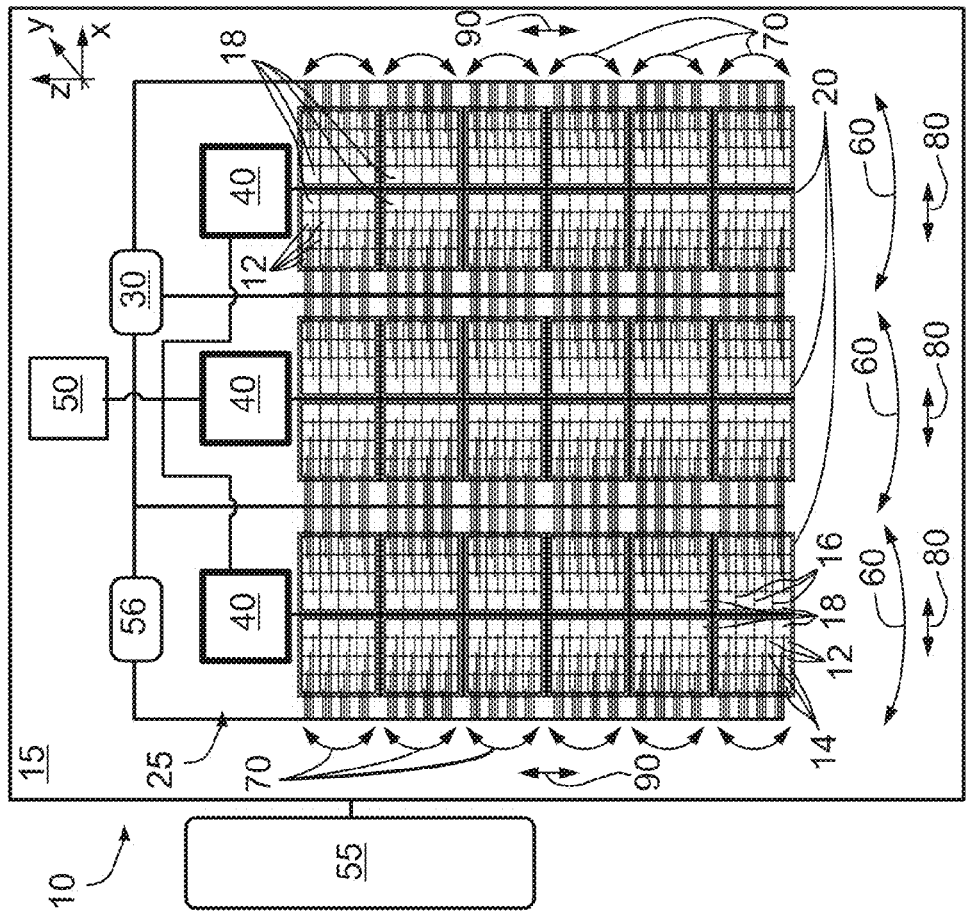
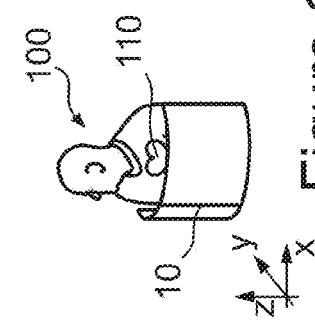
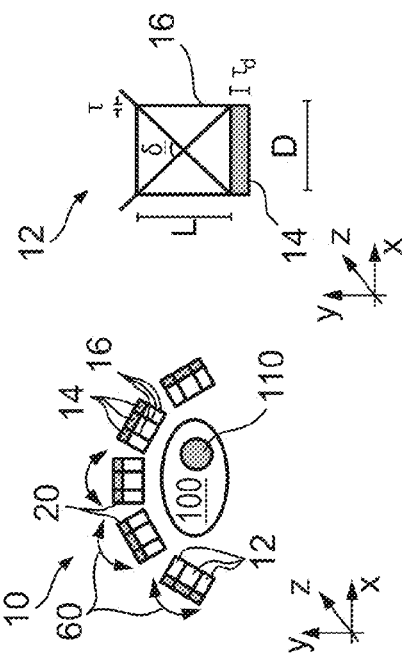
Figure 1A  Figure 1B  Figure 1C  Figure 1D

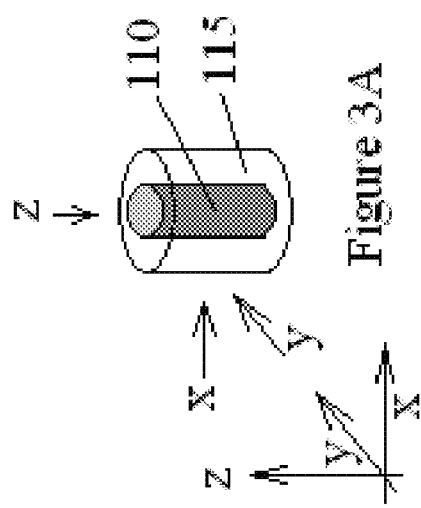
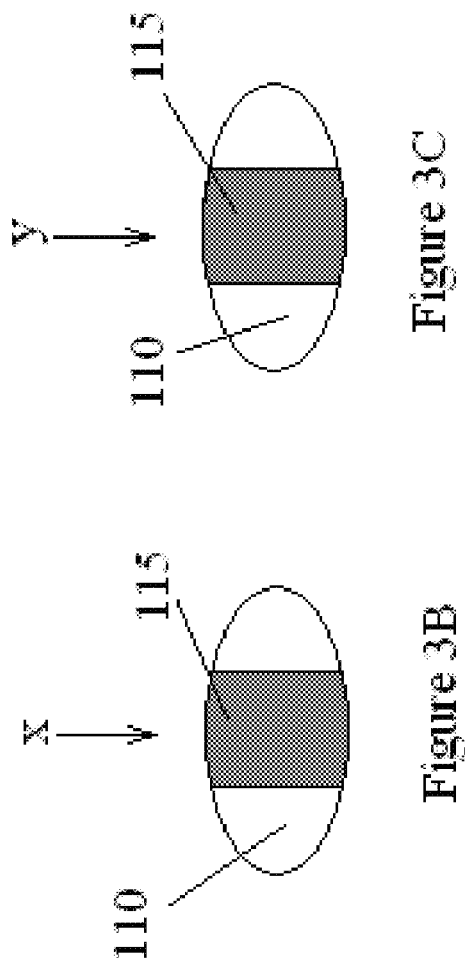
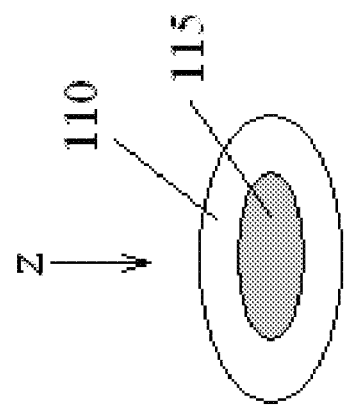

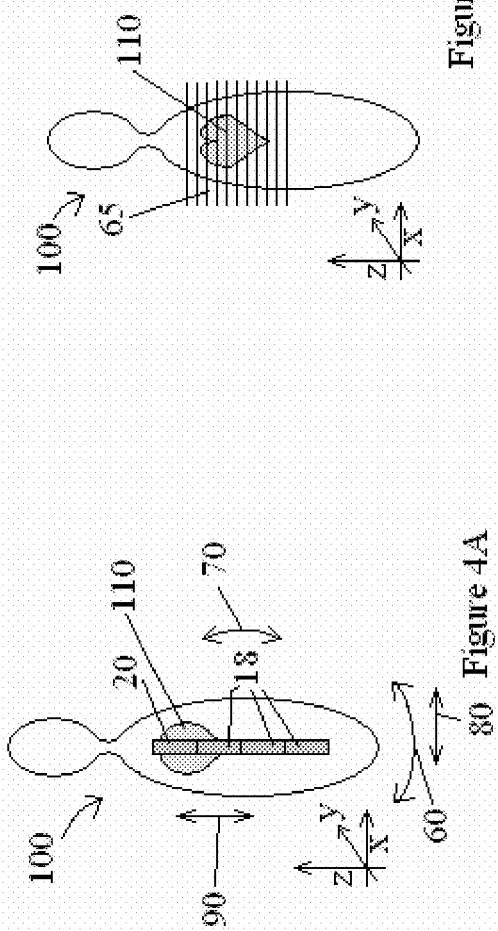
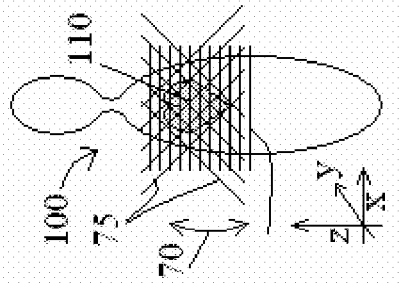
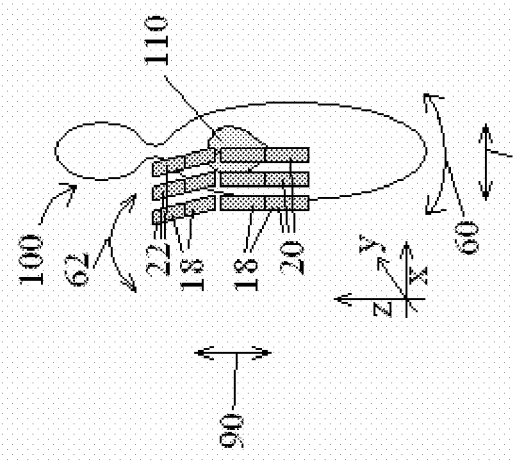
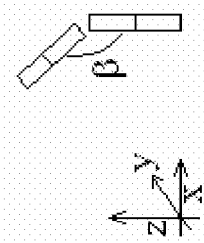
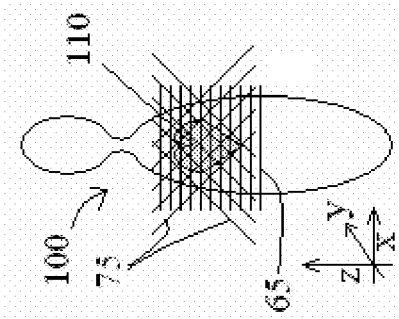

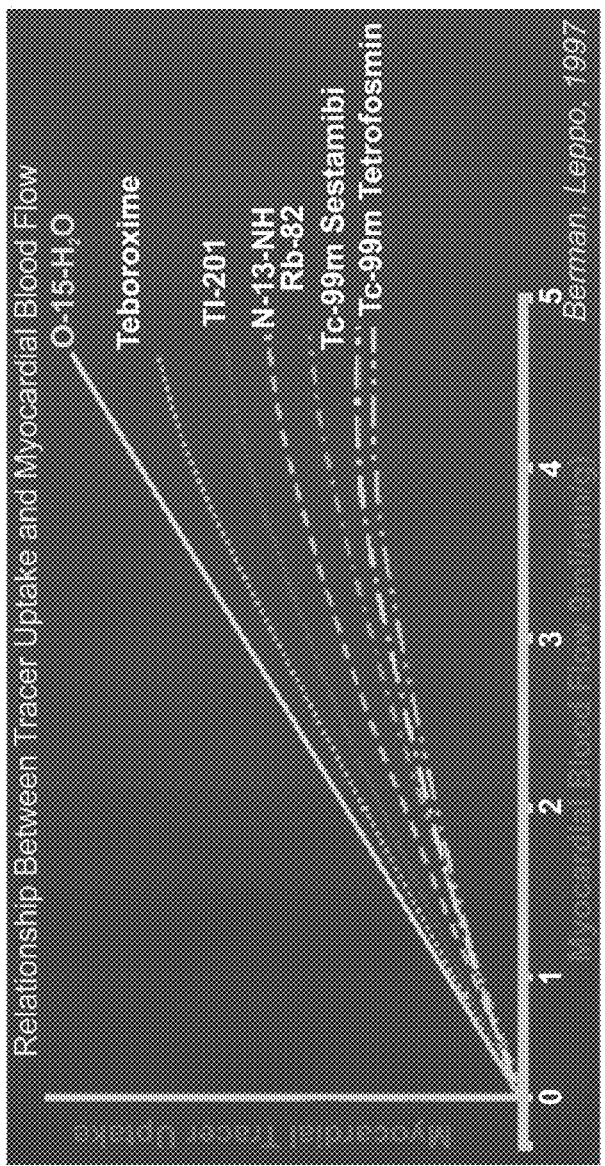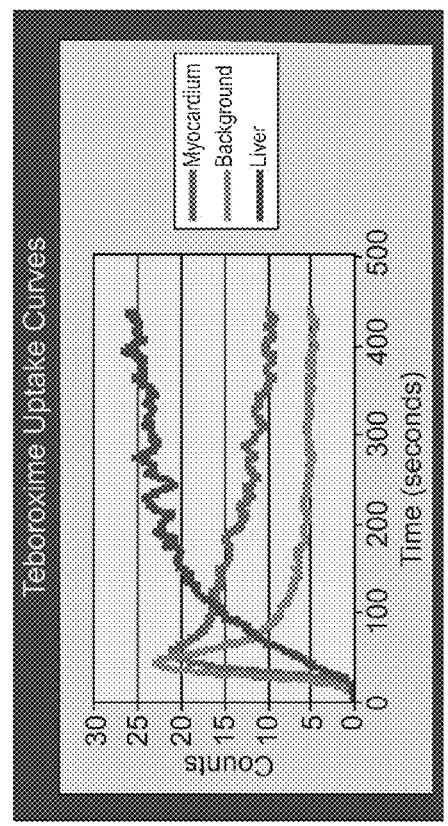
Figure 5A
Figure 5B

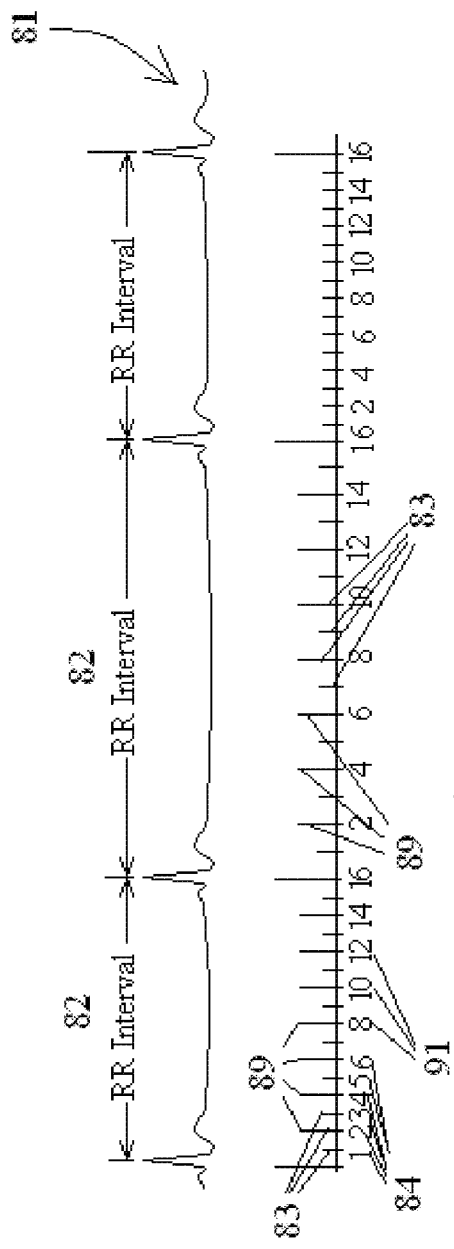
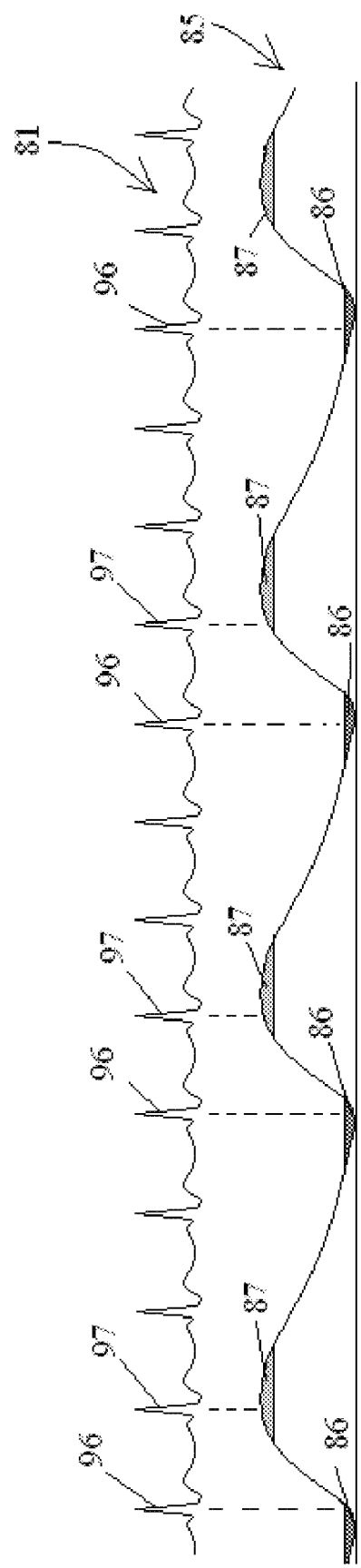
Figure 5C
Figure 5D

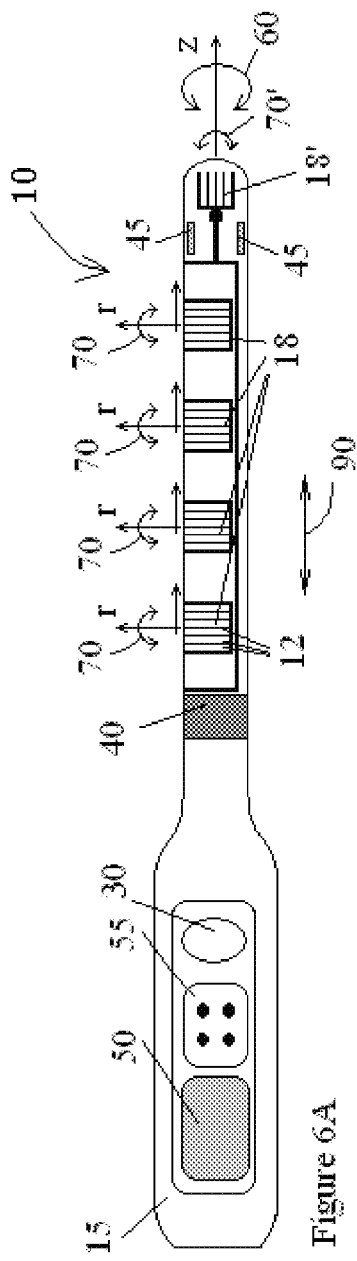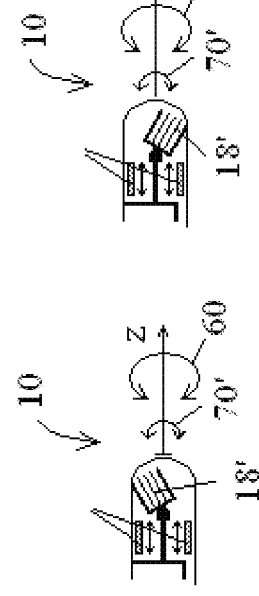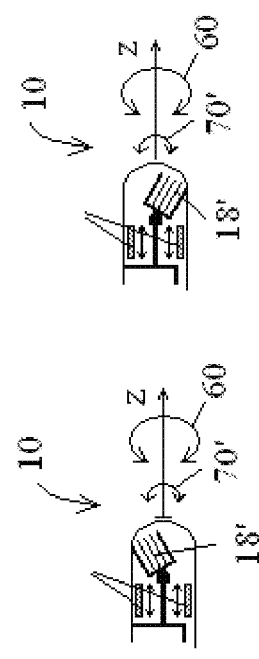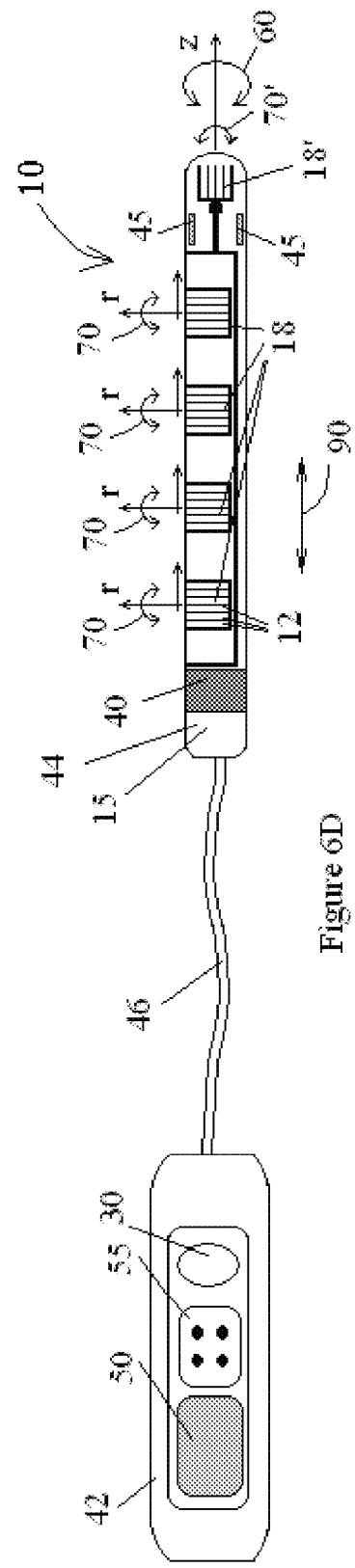
Figure 6A
Figure 6B
Figure 6C
Figure 6D

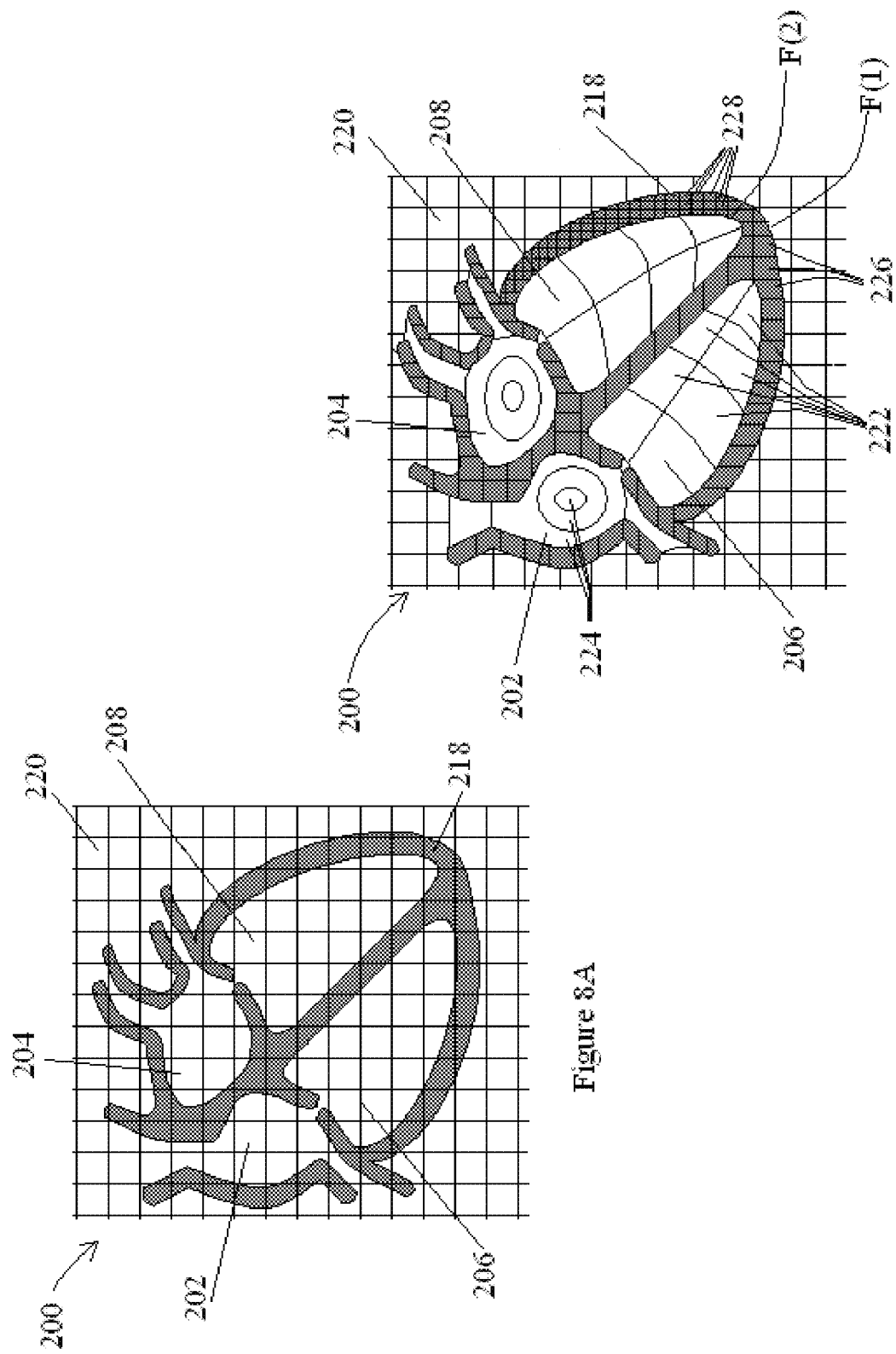

Anatomical Landmarks

- Left Ventricle (LV)
- Right Ventricle (RV)
- Left Atrium (LA)
- Right Atrium (RA)

"Movie" representation of a dynamic SPECT study (SA)

"Movie" representation of a dynamic SPECT study (SA)

Figure 10

| Time (sec) | No. of events | Average rate (MHz) |
|---|---|---|
| 0.001 | 56 | 0.056 |
| 0.002 | 369 | |
| 0.003 | 379 | 0.379 |
| 0.004 | 378 | 0.378 |
| 0.005 | 382 | 0.382 |
| 0.006 | 376 | 0.376 |
| 0.007 | 366 | 0.366 |
| 0.008 | 372 | 0.372 |
| 0.009 | 374 | 0.374 |
| 0.010 | 372 | 0.372 |
| 0.011 | 370 | 0.370 |
| 0.012 | 371 | 0.371 |
| 0.013 | 364 | 0.364 |
| 0.014 | 372 | 0.372 |
| 0.015 | 374 | 0.374 |
| 0.016 | 372 | 0.372 |
| 0.017 | 364 | 0.364 |
| 0.018 | 368 | 0.368 |
| 0.019 | 364 | 0.364 |
| 0.020 | 373 | 0.373 |
| 0.021 | 362 | 0.362 |
| 0.022 | 374 | 0.374 |
| 0.023 | 372 | 0.372 |
| 0.024 | 377 | 0.377 |
| 0.025 | 367 | 0.367 |
| 0.026 | 377 | 0.377 |
| 0.027 | 373 | 0.373 |
| 0.028 | 363 | 0.363 |
| 0.029 | 373 | 0.373 |

DYNAMIC SPECT CAMERA

RELATED APPLICATIONS

This application is a continuation of U.S. patent application Ser. No. 12/084,559 filed on Nov. 26, 2008, which is a National Phase of PCT Application No. PCT/IL2006/001291 having International Filing Date of Nov. 9, 2006.

PCT Application No. PCT/IL2006/001291 is a continuation-in-part (CIP) of PCT Application Nos. PCT/IL2006/000840 and PCT/IL2006/000834, both filed on Jul. 19, 2006, PCT Application No. PCT/IL2006/000562, filed on May 11, 2006, PCT Application No. PCT/IL2006/000059, filed on Jan. 15, 2006, PCT Application No. PCT/IL2005/001215, filed on Nov. 16, 2005, and PCT Application No. PCT/IL2005/001173, filed on Nov. 9, 2005.

PCT Application No. PCT/IL2006/001291 also claims the benefit of priority from U.S. Provisional Patent Application No. 60/816,970, filed on Jun. 28, 2006, U.S. Provisional Patent Application Nos. 60/800,846 and 60/800,845, both filed on May 17, 2006, U.S. Provisional Patent Application No. 60/799,688, filed on May 11, 2006, U.S. Provisional Patent Application No. 60/763,458, filed on Jan. 31, 2006, U.S. Provisional Patent Application No. 60/754,199, filed on Dec. 28, 2005, U.S. Provisional Patent Application Nos. 60/750,597 and 60/750,334, both filed on Dec. 15, 2005, U.S. Provisional Patent Application No. 60/750,287, filed on Dec. 13, 2005, and U.S. Provisional Patent Application No. 60/741,440, filed on Dec. 2, 2005.

PCT Application No. PCT/IL2006/001291 also claims the benefit of priority from Israel Patent Application No. 172349, filed on Nov. 27, 2005.

PCT Application No. PCT/IL2005/001173 is a continuation-in-part (CIP) of PCT Application Nos. PCT/IL2005/000575, and PCT/IL2005/000572, both filed on Jun. 1, 2005, and PCT Application No. PCT/IL2005/000048, filed on Jan. 13, 2005.

PCT Application No. PCT/IL2005/001173 also claims the benefit of priority from U.S. Provisional Patent Application Nos. 60/720,652 and 60/720,541, both filed on Sep. 27, 2005, U.S. Provisional Patent Application No. 60/720,034, filed on Sep. 26, 2005, U.S. Provisional Patent Application No. 60/702,979, filed on Jul. 28, 2005, U.S. Provisional Patent Application Nos. 60/700,753 and 60/700,752, both filed on Jul. 20, 2005, U.S. Provisional Patent Application Nos. 60/700,318, 60/700,317, and 60/700,299, filed on Jul. 19, 2005, U.S. Provisional Patent Application No. 60/691,780, filed on Jun. 20, 2005, U.S. Provisional Patent Application No. 60/675,892, filed on Apr. 29, 2005, U.S. Provisional Patent Application No. 60/648,690, filed on Feb. 2, 2005, U.S. Provisional Patent Application No. 60/648,385, filed on Feb. 1, 2005, U.S. Provisional Patent Application No. 60/640,215, filed on Jan. 3, 2005, U.S. Provisional Patent Application No. 60/636,088, filed on Dec. 16, 2004, U.S. Provisional Patent Application No. 60/635,630, filed on Dec. 14, 2004, U.S. Provisional Patent Application No. 60/632,515, filed on Dec. 3, 2004, U.S. Provisional Patent Application No. 60/632,236, filed on Dec. 2, 2004, U.S. Provisional Patent Application No. 60/630,561, filed on Nov. 26, 2004, U.S. Provisional Patent Application No. 60/628,105, filed on Nov. 17, 2004, and U.S. Provisional Patent Application No. 60/625,971, filed on Nov. 9, 2004.

PCT Application No. PCT/IL2005/001173 also claims the benefit of priority from Israel Patent Application No. 171346, filed on Oct. 10, 2005.

PCT Application No. PCT/IL2005/000575 claims the benefit of priority from U.S. Provisional Patent No. 60/575,369, filed on Jun. 1, 2004.

U.S. patent application Ser. No. 12/084,559 is also a continuation-in-part (CIP) of U.S. patent application Ser. No. 11/034,007, filed on Jan. 13, 2005, now U.S. Pat. No. 7,176,466, issued on Feb. 13, 2007, which claims the benefit of priority from U.S. Provisional Patent Application No. 60/535,830, filed on Jan. 13, 2004.

The contents of the above Applications are all incorporated herein by reference.

FIELD OF THE INVENTION

The present invention relates SPECT nuclear imaging, and particularly, to systems, methods, and cameras for single-photon-emission-computed-tomography, in list mode, with sensitivity which meets, even outperforms that of PET, in terms of speed and spatial resolution, and with a high spectral resolution not available in PET.

BACKGROUND OF THE INVENTION

Radionuclide imaging aims at obtaining an image of a radioactively labeled substance, that is, a radiopharmaceutical, within the body, following administration, generally, by injection. The substance is chosen so as to be picked up by active pathologies to a different extent from the amount picked up by the surrounding, healthy tissue in consequence, the pathologies are operative as radioactive-emission sources and may be detected by radioactive-emission imaging. A pathology may appear as a concentrated source of high radiation, that is, a hot region, as may be associated with a tumor, or as a region of low-level radiation, which is nonetheless above the background level, as may be associated with carcinoma.

A reversed situation is similarly possible. Dead tissue has practically no pick up of radiopharmaceuticals, and is thus operative as a cold region.

The mechanism of localization of a radiopharmaceutical in a particular organ of interest depends on various processes in the organ of interest such as antigen-antibody reactions, physical trapping of particles, receptor site binding, removal of intentionally damaged cells from circulation, and transport of a chemical species across a cell membrane and into the cell by a normally operative metabolic process. A summary of the mechanisms of localization by radiopharmaceuticals is found in http://www.lunis.luc.edu/nucmed/tutorial/radpharm/i.htm.

The particular choice of a radionuclide for labeling antibodies depends upon the chemistry of the labeling procedure and the isotope nuclear properties, such as the number of gamma rays emitted, their respective energies, the emission of other particles such as beta or positrons, the isotope half-life, and the decay scheme.

In PET imaging, positron emitting radio-isotopes are used for labeling, and the imaging camera detects coincidence photons, the gamma pair of 0.511 Mev, traveling in opposite directions. Each coincident detection defines a line of sight, along which annihilation takes place. As such, PET imaging collects emission events, which occurred in an imaginary tubular section enclosed by the PET detectors. A gold standard for PET imaging is PET $NH_3$ rest myocardial perfusion imaging with N-13-ammonia ($NH_3$), at a dose level of 740 MBq, with attenuation correction. Yet, since the annihilation gamma is of 0.511 Mev, regardless of the radio-isotope, PET imaging does not provide spectral information, and does not differentiate between radio-isotopes.

In SPECT imaging, primarily gamma emitting radio-isotopes are used for labeling, and the imaging camera is designed to detect the actual gamma emission, generally, in an energy range of approximately 11-511 KeV. Generally, each detecting unit, which represents a single image pixel, has a collimator that defines the solid angle from which radioactive emission events may be detected.

Because PET imaging collects emission events, in the imaginary tubular section enclosed by the PET detectors, while SPECT imaging is limited to the solid collection angles defined by the collimators, generally, PET imaging has a higher sensitivity and spatial resolution than does SPECT. Therefore, the gold standard for spatial and time resolutions in nuclear imaging are defined for PET. For example, there is a gold standard for PET imaging for at rest myocardial perfusion with N-13-ammonia ($NH_3$), at a dose of 740 MBq with attenuation correction."

Conventional SPECT cameras generally employ an Anger camera, in which a single-pixel scintillation detector, such as NaI(Tl), LSO, GSO, CsI, CaF, or the like, is associated with a plurality of photomultipliers. Dedicated algorithms provide a two dimensional image of the scintillations in the single pixel scintillation detector. There are several disadvantages to this system, for example:

1. the dedicated algorithms associated with the single pixel cannot reach the accuracy of a two-dimensional image of a plurality of single pixel detectors;

2. the single-pixel detector is a rigid unit, which does not have the flexibility of motion of a plurality of small detectors, each with independent motion; and 3. a single hot spot may cause the single pixel detector of the Anger camera to saturate, whereas when a plurality of single pixel detectors is employed, saturation is localized to a few pixels and does not affect the whole image.

Other SPECT cameras which employ a plurality of single pixel detectors are also known.

U.S. Pat. No. 6,628,984, to Weinberg, issued on Sep. 30, 2003 and entitled, "Hand held camera with tomographic capability," describes a tomographic imaging system, which includes a moveable detector or detectors capable of detecting gamma radiation; one or more position sensors for determining the position and angulation of the detector(s) in relation to a gamma ray emitting source; and a computational device for integrating the position and angulation of the detector(s) with information as to the energy and distribution of gamma rays detected by the detector and deriving a three dimensional representation of the source based on the integration. A method of imaging a radiation emitting lesion located in a volume of interest also is disclosed.

U.S. Pat. No. 6,242,743, to DeVito, et al., issued on Jun. 5, 2001 and entitled, "Non-orbiting tomographic imaging system," describes a tomographic imaging system which images ionizing radiation such as gamma rays or x rays and which: 1) can produce tomographic images without requiring an orbiting motion of the detector(s) or collimator(s) around the object of interest, 2) produces smaller tomographic systems with enhanced system mobility, and 3) is capable of observing the object of interest from sufficiently many directions to allow multiple time-sequenced tomographic images to be produced. The system consists of a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with high-resolution collimators in a combination of application-specific acquisition geometries and non-orbital detector module motion sequences composed of tilting, swiveling and translating motions, and combinations of such motions. Various kinds of module geometry and module or collimator motion sequences are possible, and several combinations of such geometry and motion are shown. The geometric configurations may be fixed or variable during the acquisition or between acquisition intervals. Clinical applications of various embodiments of U.S. Pat. No. 6,242,743 include imaging of the human heart, breast, brain or limbs, or small animals. Methods of using the non-orbiting tomographic imaging system are also included.

U.S. Pat. No. 5,939,724, to Eisen, et al., issued on Aug. 17, 1999, and entitled, "Light weight-camera head and -camera assemblies containing it," describes a light weight gamma-camera head and assemblies and kits which embody it. The gamma-camera head has a detector assembly which includes an array of room temperature, solid state spectroscopy grade detectors each associated with a collimator and preamplifier, which detectors and associated collimators and preamplifiers are arranged in parallel rows extending in a first direction and suitably spaced from each other in a second direction normal to the first direction, each of the parallel detector rows holding a plurality of detectors. The head may optionally have an electric motor for moving the detector in the second direction and optionally also in the first direction, either stepwise or continuously.

U.S. Pat. No. 6,525,320, to Juni, issued on Feb. 25, 2003, and entitled, Single photon emission computed tomography system, describes a single photon emission computed tomography system, which produces multiple tomographic images of the type representing a three-dimensional distribution of a photon-emitting radioisotope. The system has a base including a patient support for supporting a patient such that a portion of the patient is located in a field of view. A longitudinal axis is defined through the field of view. A detector module is adjacent the field of view and includes a photon-responsive detector. The detector is an elongated strip with a central axis that is generally parallel to the longitudinal axis. The detector is operable to detect if a photon strikes the detector. The detector can also determine a position along the length of the strip where a photon is detected. A photon-blocking member is positioned between the field of view and the detector. The blocking member has an aperture slot for passage of photons aligned with the aperture slot. The slot is generally parallel to the longitudinal axis. A line of response is defined from the detector through the aperture. A displacement device moves either the detector module or the photon-blocking member relative to the other so that the aperture is displaced relative to the detector and the line of response is swept across at least a portion of the field of view.

U.S. Pat. No. 6,271,525, to Majewski, et al., issued on Aug. 7, 2001, and entitled, "Mini gamma camera, camera system and method of use," describes a gamma camera, which comprises essentially and in order from the front outer or gamma ray impinging surface: 1) a collimator, 2) a scintillator layer, 3) a light guide, 4) an array of position sensitive, high resolution photomultiplier tubes, and 5) printed circuitry for receipt of the output of the photomultipliers. There is also described, a system wherein the output supplied by the high resolution, position sensitive photomultipiler tubes is communicated to: a) a digitizer and b) a computer where it is processed using advanced image processing techniques and a specific algorithm to calculate the center of gravity of any abnormality observed during imaging, and c) optional image display and telecommunications ports.

U.S. Pat. No. 6,271,524, to Wainer, et al., issued on Aug. 7, 2001 and entitled, "Gamma ray collimator," describes a gamma ray collimator assembly comprising collimators of different gamma ray acceptance angles. For example, the acceptance angle of a first collimator may be between 0.2 and 5 degrees, and the acceptance angle of a second collimator may be between about 5 and 30 degrees.

U.S. Pat. No. 6,212,423, to Krakovitz, issued on Apr. 3, 2001 and entitled, "Diagnostic hybrid probes," describes a hybrid nuclear and ultrasonic probe, comprising a cylindrical outer casing surrounding a nuclear probe, which comprises two scintillator plates intersecting perpendicularly, each of the scintillator plates having a plurality of parallel collimators; and an ultrasonic probe situated between said casing at the intersection of said scintillator plates.

List mode data acquisition is known in PET studies, and enables the determination of coincidence. It relates to recording every radiation event together with data pertinent to that event, which includes:

i. the time the radiation event impinged upon a detector pixel, with respect to a clock, with respect to a time bin, or with respect to another time definition, for example, a time interval between two clock signals; and ii. the detector pixel location with respect to a coordinate system, at the time of the impinging.

The knowledge of time and location enables the determination of coincidence counts, namely photon counts that arrive substantially simultaneously, 180 degrees apart.

The time and location data may be stamped onto the radiation-event data packet, for example, as a header or as a footer, or otherwise associated with the radiation-event data packet, as known.

The time-stamped data available in PET studies may further be used for perfusion studies, where the timing of physiological processes of short durations, that is, durations shorter than about half the time span between heartbeats, is important. Perfusion studies usually involve a sequence of continuous acquisitions, each of which may represent data acquisition duration of about 10-30 seconds, although longer durations are sometimes employed. Data from each of the frames is independently reconstructed to form a set of images which can be visualized and used to estimate physiological parameters. This approach involves selection of the set of acquisition times, where one must choose between collecting longer scans with good counting statistics but poor temporal resolution, or shorter scans that are noisy but preserve temporal resolution.

US Patent Application 2003010539, to Tumer, et al., published on Jun. 5, 2003, and entitled, "X-ray and gamma ray detector readout system," describes a readout electronics scheme, under development for high resolution, compact PET (positron emission tomography) imagers, using time tagging, based on LSO (lutetium ortho-oxysilicate, $Lu_2SiO_5$) scintillator and avalanche photodiode (APD) arrays.

There is some work relating to timing data in SPECT systems, employing Anger cameras.

U.S. Pat. No. 5,722,405, to Goldberg, issued on Mar. 3, 1998, and entitled, "Method and apparatus for acquisition and processing of event data in semi list mode," describes a system for acquisition, processing and display of gated SPECT imaging data for use in diagnosing Coronary Artery Disease (CAD) in nuclear medicine, employing an Anger camera, and provides a physician with two parameters for evaluating CAD: information relating to the distribution of blood flow within the myocardium (perfusion) and information relating to myocardium wall motion (function). One aspect provides the physician with a display of functional images representing quantitative information relating to both perfusion and function with respect to selected regions of interest of the subject heart at end-diastole and end-systole segments of the cardiac cycle. The functional display consists of arcs of varied width depending on wall motion and color coded to illustrate degrees of myocardial perfusion for different pie shaped sections of a selected region of interest within a given short axis slice of reconstructed volume data. Another aspect provides a series of display images allowing facilitated access, display, and comparison of the numerous image frames of the heart that may be collected during gated SPECT sessions. U.S. Pat. No. 5,722,405 also teaches the ability to define and recall parameter files representative of data acquisition and processing parameters and protocol for use in gated SPECT studies and includes a semi-list processing mode to increase efficiency of data acquisition within a camera computer system.

U.S. Pat. No. 7,026,623, to Oaknin, et al., issued on Apr. 11, 2006, and entitled, "Efficient single photon emission imaging," describes a method of diagnostic imaging in a shortened acquisition time for obtaining a reconstructed diagnostic image of a portion of a body of a human patient who was administered with dosage of radiopharmaceutical substance radiating gamma rays, using SPECT and an Anger camera. The method comprises acquiring photons emitted from said portion of the body, by means of a detector capable of converting the photons into electric signals, wherein the total time of photon acquiring is substantially shorter than the clinically acceptable acquisition time; processing said electric signals by a position logic circuitry and thereby deriving data indicative of positions on said photon detector crystal, where the photons have impinged the detector; and reconstructing an image of a spatial distribution of the pharmaceutical substance within the portion of the body by iteratively processing said data. For example, the method includes effective acquisition time of less than 10 minutes, or less than 8 minutes, and acquiring photons in a list-mode procedure.

SUMMARY OF THE INVENTION

The present invention relates to a dynamic SPECT camera, which comprises, a plurality of single-pixel detectors, a timing mechanism, in communication with each single-pixel detector, configured for enabling time-binning of the radioactive emissions impinging upon each single-pixel detector to time periods not greater than substantially 30 seconds, and a position-tracker, configured for providing information on the position and orientation of each single-pixel detector, with respect to the overall structure, substantially at all times, during the individual motion, the dynamic SPECT camera being configured for acquiring a tomographic reconstruction image of a region of interest of about 15×15×15 cubic centimeters, during an acquisition time of 30 seconds, at a spatial resolution of at least 10×10×10 cubic millimeter. The dynamic camera is further configured for very short damping time, when in stop and shoot acquisition mode and may further acquire images in a stationary mode, with no motion. It is further configured for time binning at dynamically varying time-bin lengths, dynamically determining a spectral energy bin for each single-pixel detector, and constructing and employing an anatomic system of voxels in the imaging and reconstruction.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 2A:
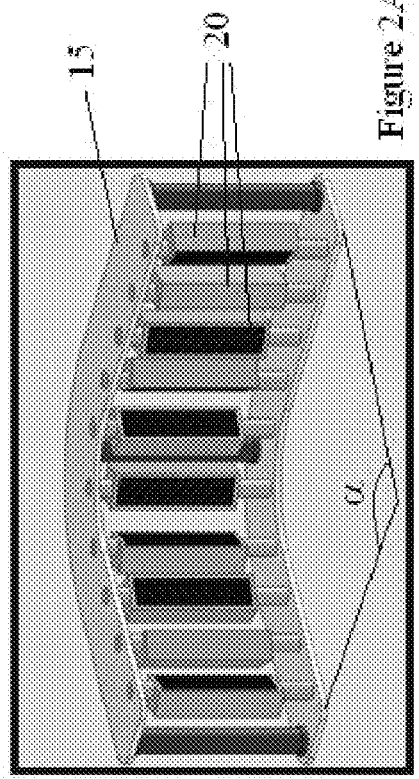
Figure 2B:
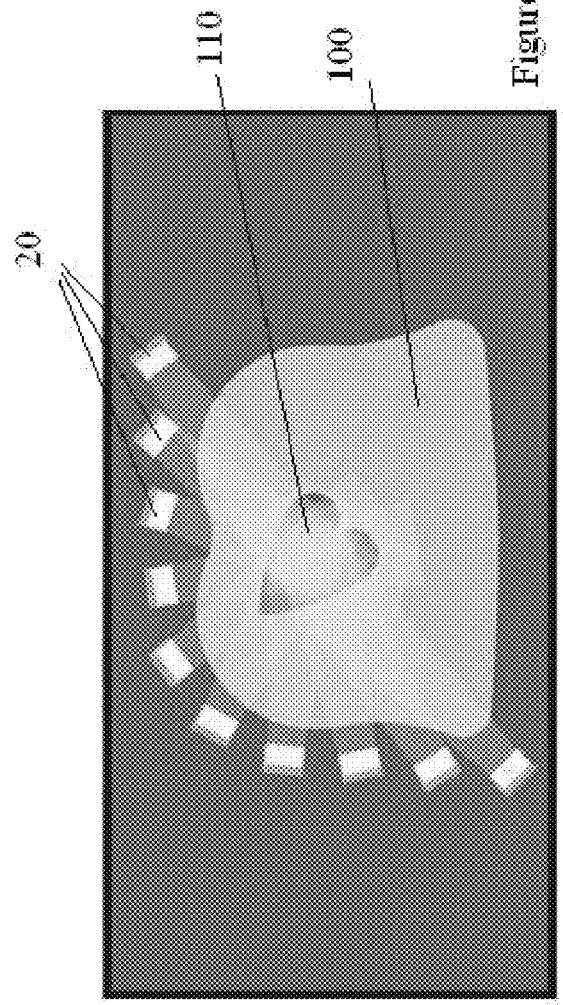

FIGS. 1A-1D schematically illustrate a dynamic SPECT camera, in accordance with embodiments of the present invention;

FIGS. 2A and 2B schematically illustrate the camera structure with the assemblies, in accordance with an embodiment of the present invention.

FIGS. 3A-3D schematically illustrate viewing positions, in accordance with embodiments of the present invention.

FIGS. 4A-4F schematically illustrate stereo views and cross views, in accordance with embodiments of the present invention.

Figure 7:
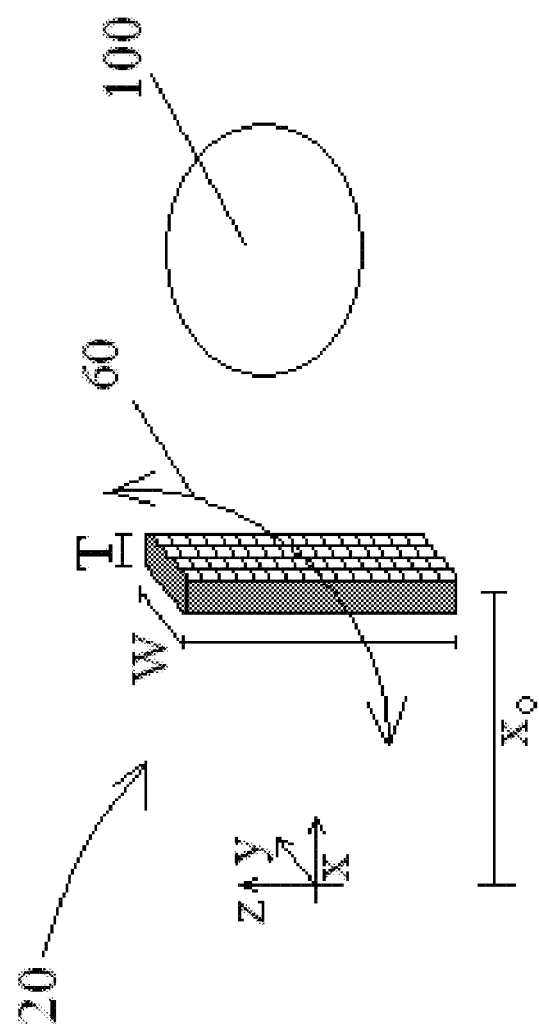
Figure 11:
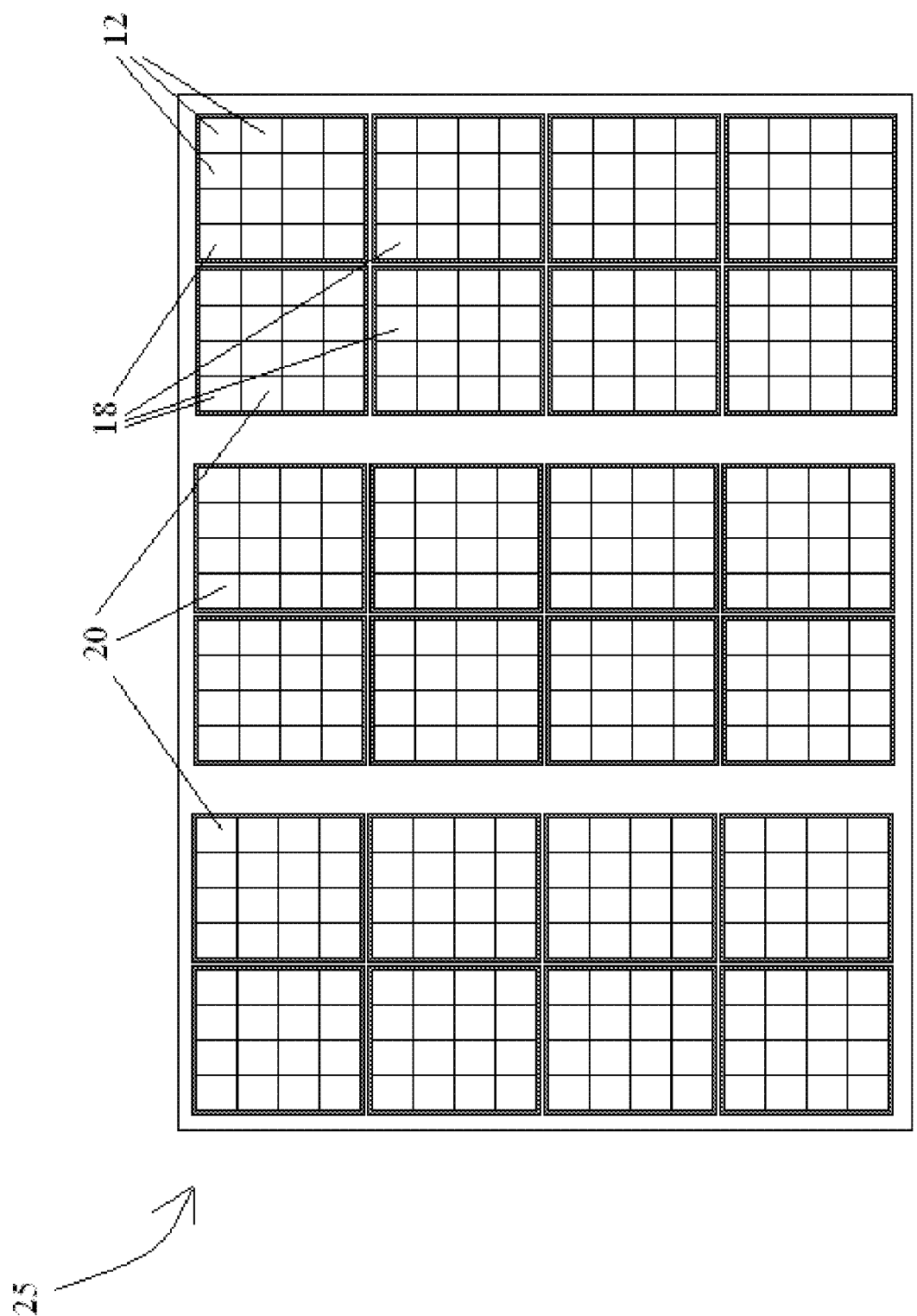
Figure 12:
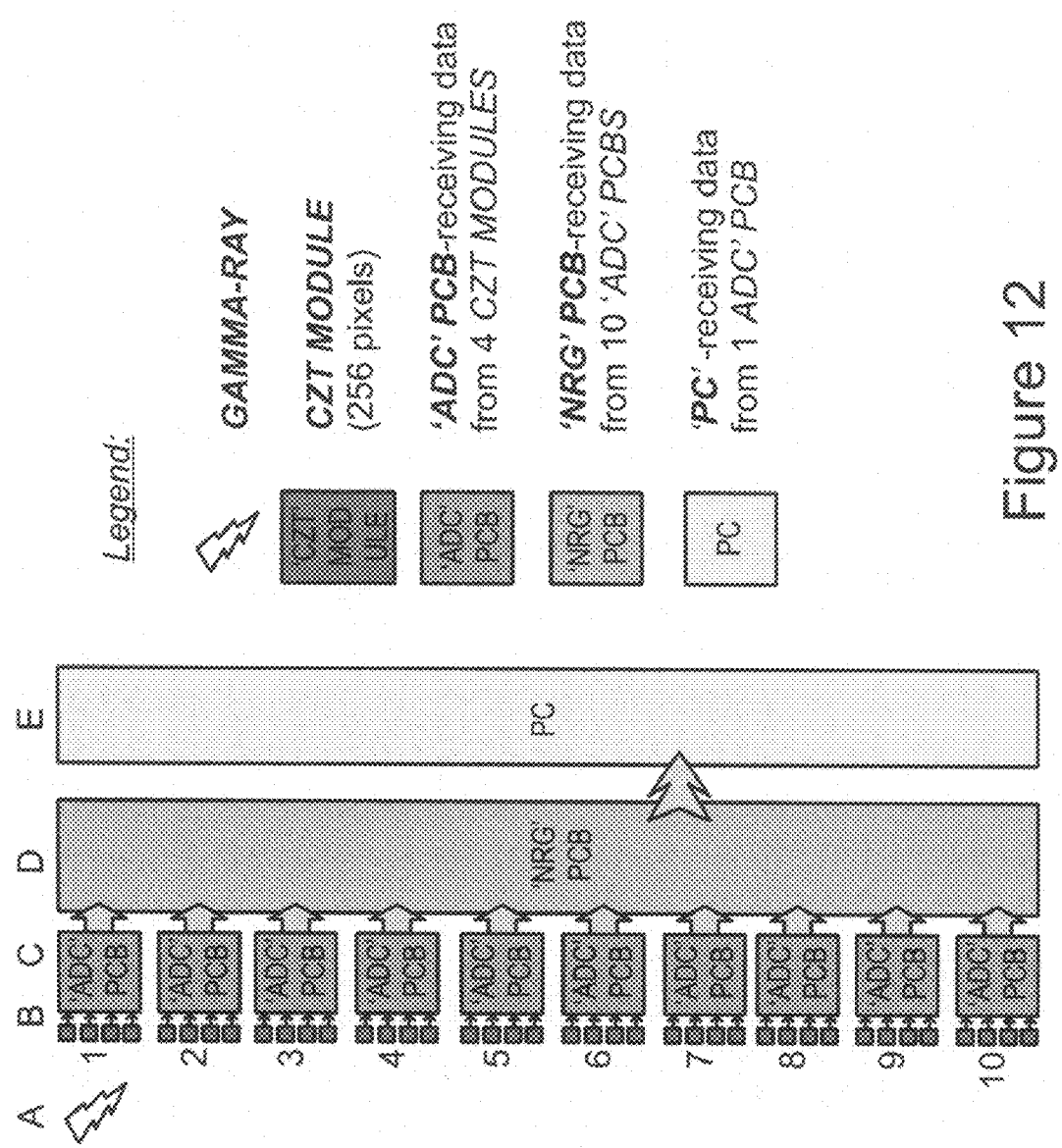

FIGS. 5A and 5B illustrate experimental radiopharmaceutical data, as known;

FIGS. 5C-5F illustrate cardiac gating, in accordance with embodiments of the present invention;

FIG. 6A-6I illustrate an intracorporeal dynamic SPECT camera, in accordance with embodiments of the present invention;

FIG. 7 illustrates assembly damping parameters, in accordance with embodiments of the present invention;

FIGS. 8A and 8B schematically illustrate grid and anatomical constructions of voxels, in accordance with embodiments of the present invention;

FIGS. 9A-9J present experimental data, obtained by the dynamic SPECT camera, in accordance with embodiments of the present invention;

FIG. 10 presents experimental data, obtained by the dynamic SPECT camera, in accordance with embodiments of the present invention;

FIG. 11 illustrates components of the dynamic SPECT camera, in accordance with embodiments of the present invention; and FIG. 12 illustrates an electrical scheme, in accordance with embodiments of the present invention.

DESCRIPTION OF THE PREFERRED EMBODIMENTS

The present invention relates to a dynamic SPECT camera, which comprises, a plurality of single-pixel detectors, a timing mechanism, in communication with each single-pixel detector, configured for enabling time-binning of the radioactive emissions impinging upon each single-pixel detector to time periods not greater than substantially 30 seconds, and a position-tracker, configured for providing information on the position and orientation of each single-pixel detector, with respect to the overall structure, substantially at all times, during the individual motion, the dynamic SPECT camera being configured for acquiring a tomographic reconstruction image of a region of interest of about 15×15×15 cubic centimeters, during an acquisition time of 30 seconds, at a spatial resolution of at least 10×10×10 cubic millimeter. The dynamic camera is further configured for very short damping time, when in stop and shoot acquisition mode and may further acquire images in a stationary mode, with no motion. It is further configured for time binning at dynamically varying time-bin lengths, dynamically determining a spectral energy bin for each single-pixel detector, and constructing and employing an anatomic system of voxels in the imaging and reconstruction.

The principles and operation of the dynamic SPECT camera according to aspects of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Dynamic SPECT Camera

Design Description of the Dynamic SPECT Camera

An aspect of the present invention relates to a dynamic SPECT camera, with temporal and spatial resolutions which meet, even outperform those of PET, and with a high spectral resolution not available in PET.

Temporal resolution, as used herein, relates to a minimal acquisition time for a tomographic reconstruction image of a predetermined volume, for example 15×15×15 cubic centimeters, and predetermined spatial resolution, for example, 10×10×10 cubic millimeters. The minimal acquisition time may be, for example, 30 seconds, 10 seconds, or 1 second.

Reference is now made to FIGS. 1A-1D, which schematically illustrate a dynamic SPECT camera 10, in accordance with embodiments of the present invention. The dynamic SPECT camera 10 comprises:

an overall structure 15, which defines proximal and distal ends and, with respect to a body 100;

a first plurality of assemblies 20, for example, 6, 9, or 16 assemblies 20, arranged on the overall structure 15, forming an array 25 of the assemblies 20, each assembly 20 comprising:

a second plurality of detecting units 12, each detecting unit 12 including:
a single-pixel detector 14, for detecting radioactive emissions; and
a dedicated collimator 16, attached to the single-pixel detector 14, at the proximal end thereof, for defining a solid collection angle δ for the detecting unit 12.

Additionally, each assembly 20 comprises an assembly motion provider 40, configured for providing the assembly 20 with individual assembly motion, with respect to the overall structure 15, during the acquisition of radioactive-emission data for a tomographic image.

The dynamic SPECT camera 10 further includes:

a timing mechanism 30, in communication with each single-pixel detector 14, configured for enabling time-binning of the radioactive emissions impinging upon each single-pixel detector 14 to time periods not greater than substantially 30 seconds; and a position tracker 50, configured for providing information on the position and orientation of each detecting unit 12, with respect to the overall structure 15, substantially at all times, during the individual assembly motion.

The dynamic SPECT camera 10 is configured for acquiring a tomographic reconstruction image of a region of interest of about 15×15×15 cubic centimeters, for example, of a target organ 110, such as a heart or a stomach, during an acquisition period no greater than 300 seconds, at a spatial resolution of at least 10×10×10 cubic millimeters.

It will be appreciated that the time period may be no greater than 200 seconds, 100 seconds, 60 seconds, 30 seconds, 10 seconds, or 1 second.

Additionally, the dynamic SPECT camera 10 is configured for acquiring a series of tomographic reconstruction images of a region of interest, as a function of time, at a rate of at least a tomographic reconstruction image every 300 seconds.

Again, the rate may further be every 200 seconds, 100 seconds, 60 seconds, 30 seconds, 10 seconds, or 1 second.

In accordance with embodiments of the present invention, the individual assembly motion may be, for example, an assembly oscillatory sweeping motion, as described by an arrow 60. Additionally or alternatively, the individual assembly motion may be a first oscillatory lateral motion, as described by an arrow 80. Additionally or alternatively, the individual assembly motion may be a second oscillatory lateral motion, orthogonal to the first, as described by an arrow 90. Thus, the assembly motion provider 40 may comprise between one and three motion providing units, for the different assembly motions.

Alternatively, the individual assembly motion is an assembly oscillatory sweeping motion, as described by an arrow 60, while the array 25 moves with either the first or the second oscillatory lateral motions, described by the arrows 80 and 90, or with both.

Additionally, the detecting units 12 may be grouped into square or rectangular blocks 18, for example, of 4×4 detecting units 12, as seen in FIG. 1A, or of 16×16, 64×64, 64×128 or another number of detecting units 12. Furthermore, the blocks 18 may be provided with individual block oscillatory sweeping motion, as described by an arrow 70, with respect to the overall structure 15, during the acquisition of radioactive-emission data for a tomographic image. Preferably, the block oscillatory sweeping motion is orthogonal to, or at an angle to the assembly oscillatory sweeping motion, described by the arrow 60. Thus, the assembly motion provider 40 may further comprise a dedicated block motion providing unit, in communication with each block of an assembly.

A control unit 55 may be integrated with the dynamic SPECT camera 10, so as to form a single physical unit, or in communication with the dynamic SPECT camera 10.

A spectral selection mechanism 56, in communication with each of the detecting unit 12, is discussed hereinbelow, under the heading, "dynamically varying spectral bins."

The body 100 may be a human or an animal, and the region of interest, or the target organ 110 may be a heart, a brain, a breast, a stomach, a GI tract, a colon, a prostate, a uterus, a cervix, a vagina, a throat, a gland, a lymph node, a portion of skin, a portion of bone, portion of another tissue, or another body portion.

As seen in FIGS. 1A and 1B, a reference x;y;z coordinate system illustrates a preferred orientation of the dynamic SPECT camera 10 with respect to the body 100, wherein z runs along a length of the body 100. For convenience, the assembly axis along the assembly length will be referred to as the assembly longitudinal axis, and the assembly axis along the assembly width will be referred to as the assembly traverse axis.

Preferably, the assemblies 20 are long and narrow columns, arranged longitudinally against the body 100, wherein the oscillatory sweeping motion, described by an arrow 60, is about the z-axis. It will be appreciated that other arrangements are similarly possible.

As seen in FIG. 1C, illustrating a cross-sectional view in the x-y plane, preferably, the assemblies 20 are arranged in an arc or an arc-like structure, about the body 100, maintaining a shape that follows the body contours, so as to keep as close as possible to the body 100.

FIG. 1D provides details of the detecting unit 12. The collimator has a length L, a collection angle δ, and a septa thickness τ. The single pixel detector is preferably a square of sides D and a detector thickness $\tau_d$.

Preferred dimensions for the detecting unit 12 may be, for example, 2.46 mm×2.46 mm, and the solid collection angle δ may be at least 0.005 steradians. Generally, there may be 16×64 detecting units 12 per block 18.

The detector 14 is preferably, a room temperature, solid-state CdZnTe (CZT) detector, which is among the more promising that is currently available. It may be obtained, for example, IMARAD IMAGING SYSTEMS LTD., of Rehovot, ISRAEL, 76124, www.imarad.com, or from eV Products, a division of II-VI Corporation, Saxonburg Pa., 16056, or from or from another source. Alternatively, another solid-state detector such as CdTe, HgI, Si, Ge, or the like, or a combination of a scintillation detector (such as NaI(Tl), LSO, GSO, CsI, CaF, or the like) and a photomultiplier, or another detector as known, may be used, preferably with a photomultiplier tube for each single-pixel detector 14 and collimator 16, for accurate spatial resolution.

Reference is further made to FIGS. 2A and 2B which schematically illustrate the structure 15 with the assemblies 20, in accordance with an embodiment of the present invention. As seen, the assemblies 20 are arranged in an arc of an angle α, around the body 100, and move in the assembly oscillatory sweeping motion, about the z-axis, so as to provide a plurality of views of the heart 110, from many positions, along the x-y plane.

As seen in FIGS. 2A and 2B, the dynamic camera 10 is configured for simultaneous acquisition by the assemblies 20, each scanning the same region of interest from a different viewing position, thus achieving both shorter acquisition time and better edge definitions.

Preferably, the structure 15 conforms to the contours of the body 100, so as to maintain substantial contact or near contact with the body.

The embodiment of FIGS. 2A and 2B illustrate a single type of motion-assembly oscillatory sweeping motion about the z-axis, as described by the arrow 60 (FIG. 1A). In some cases, additional motions or views from additional directions may be desirous, as illustrated in FIGS. 3A-3D, hereinbelow.

Reference is further made to FIGS. 3A-3D, which schematically illustrate viewing positions, in accordance with embodiments of the present invention.

FIG. 3A illustrates a cylindrical target organ 110, with a cylindrical radioactive emission source 115 therein.

As seen in FIG. 3B, a view along the x-axis will observe the cylindrical radioactive emission source 115 as a bar 115.

As seen in FIG. 3C, a view along the y-axis will similarly observe the cylindrical radioactive emission source 115 as a bar 115, thus not adding new information to the view along the x axis.

It will be appreciated that in the present example, any view along the x-y plane will observe the radioactive emission source 115 as a bar 115.

As seen in FIG. 3D, a view along the z-axis will observe the cylindrical radioactive emission source 115 as a circle 115, adding new information to the views along the x and y axes.

As FIGS. 3A-3D illustrate, at times, views along two axes may be insufficient for a three-dimensional definition of an object, and it may be beneficial to include views with a component along the third axis. For the sake of definition, views along two axis will be referred to stereo views, while views that include a component of the third axis will be referred to as cross views, since they intersect the planer stereo views.

Reference is further made to FIGS. 4A-4F, which schematically illustrate stereo views and cross views, in accordance with embodiments of the present invention.

FIG. 4A illustrate the body 100 with a single assembly 20 arranged for viewing, for example, the heart 110. The assembly 20 is afforded with assembly oscillatory sweeping motion along the z-axis, as described by the arrow 60, and preferably also first and second preferably orthogonal oscillatory lateral motions, described the arrows 80 and 90, respectively.

As seen in FIG. 4B, the assembly oscillatory sweeping motion along the z-axis, described by the arrow 60, produces views 65 in the x-y planes. The first and second orthogonal oscillatory lateral motions, described the arrows 80 and 90, augment these with additional views 65 in the x-y planes. The purpose of the first and second oscillatory lateral motions is to compensate for "dead areas," that is, structural areas and other areas that do not participate in the detection, within the assembly 20 and between the assemblies 20, so as to provide complete coverage of the body 100, by the array 25 (FIG. 1A). These motions produce views substantially in the x-y plane. It will be appreciated that there is a component of viewing in a third axis, due to the solid collection angle of the collimator 16. Yet this component is rather small.

Returning to FIG. 4A, the blocks 18 of the assembly 20 may be further afforded with block oscillatory sweeping motion, described by the arrow 70 and preferably orthogonal to the assembly oscillatory sweeping motion described by the arrow 60.

As seen in FIG. 4C, the block oscillatory sweeping motion, described by the arrow 70, produces cross views 75, which supplement views 65, by providing components of the third axis, namely, the z axis. As illustrated in FIGS. 3A-3D, hereinabove, the views 75 may add additional information, not available or barely available in the views 65 along the x-y planes.

FIGS. 4D and 4F illustrate an alternative mode for acquiring the cross views 75. Accordingly, the dynamic camera 10 further includes assemblies 22, arranged at an angle β to the assemblies 20, and moving with an assembly oscillatory sweeping motion, described by an arrow 62, so as to provide the cross views 75.

The Position Tracker 50

The position tracker 50 is configured for providing information on the position and orientation of each detecting unit 12, with respect to the overall structure 15, substantially at all times, during the individual assembly motion.

In accordance with a preferred embodiment of the present invention, the position tracker 50 relates to software and (or) hardware that receive information from the motion provider 40 and calculate the position and orientation of each detecting unit 12, based on that information. Preferably, the calculation is performed within the control unit 55.

Alternatively, position sensors, as known, may be used for determining the position and angular orientation of each detecting unit 12.

Alternatively still, a combination of information from the motion provider 40 and position sensors may be employed.

The Timing Mechanism 30

The timing mechanism 30 associates timing information with the radioactive emission data impinging the single-pixel detectors 14 of the detecting units 12. Preferably the timing mechanism 30 includes a single clock used for all of the single-pixel detectors 14 in the dynamic SPECT camera 10, so that timing information is synchronized for the camera as a whole. The timing information is collected at the single-pixel level, so that time-binning may be performed for the emission data collected by each pixel. Exemplary methods for associating timing information with the radioactive emission data include:

1) Time stamping—Each event, impinging on a given single-pixel detector 14 at a given time is stamped with a time of detection and a pixel identification. Stamping may be performed by any manner known in the art, for example as a data packet header or footer. The time-stamped, pixel stamped radioactive emission data may be binned, per time and per pixel, by the control unit 55.

2) Time binning—In an alternate approach, timing information is provided for a cumulative count collected from each single-pixel detector 14 over a fixed time interval, for example, 0.001 seconds, 1 second, or 10 seconds, rather than for individual events. Each time bin is then stamped with a time stamp or sequential number and a pixel identification. One technique for performing time binning, is to insert a periodic clock pulse into the data stream. The interval between the clock pulses equals the minimum bin length. Thus, periodic pulses every 0.001 seconds may lead to bin lengths of 0.001 seconds or greater, for example, 1 second, or 10 seconds.

Time Scale Considerations

Dynamic studies, aimed at obtaining kinetic parameters, require the acquisition of full reconstructed images at a rate that is no greater than about half the frequency of the sampled kinetic parameter. For example, for adult humans, blood circulates through the body at a rate of about 1 cycle per minute. Thus, sampling a process affected by blood circulation should take place at a rate of at least two samplings per minute. Preferably, sampling should be at a much greater rate, for example, 6 samplings or 10 samplings per minute—that is, about every 10 seconds or about every 6 seconds.

Additionally, based on FIGS. 5A and 5B, according to Garcia et al. (Am. J. Cardiol. 51$^{st}$ Annual Scientific Session, 2002), showing physiological behavior of different radiopharmaceuticals, dynamic studies for Tc-99m teboroxime are best performed within about the first 100 seconds after administration, and better still, within the first 60 seconds after administration.

Moreover, based on FIGS. 5A and 5B, the dynamic behavior of a radiopharmaceutical in the body, varies as a function of time, depending on the radiopharmaceutical and on the time elapsed since its administration. For example, myocardial perfusion of Tc-99m teboroxime shows a very steep uptake between about the first 10-15 seconds and the first 50-60 seconds, followed by a more gradual washout, after the first 60 seconds. The rate of sampling of Tc-99m teboroxime, during the first 60 seconds after administration should be adjusted to the very steep uptake, for example, a sampling rate of every second. For radiopharmaceutical with a slower dynamic behavior, a slower rate may be sufficient.

It will be appreciated that a dynamic analysis requires precise knowledge of the time of administration.

Obtaining the Time of Administration of a Radiopharmaceutical

As noted hereinabove, precise knowledge of the time of administration of a radiopharmaceutical is important both in order to evaluate physiological processes made visible by the radiopharmaceutical, with respect to the time of the radiopharmaceutical's entry to the body and in order to perform the evaluation at an optimal period, with respect to the radiopharmaceutical's cycle in the body.

There are several methods for acquiring precise knowledge of the time of administration of the radiopharmaceutical, as follows:

1. providing communication means between an administration device, for example, a syringe or an IV device, and the dynamic SPECT camera 10, and communicating the precise time of administration, vis a vis a clock, by the administration device to the dynamic SPECT camera 10. This method may be employed for example, when administration takes place when the patient is positioned at the dynamic SPECT camera 10, for imaging.
2. providing communication means between the administration device, the dynamic SPECT camera 10, and a third unit, for example, a control system or a hospitals ERP system, communicating the precise time of administration, vis a vis a clock, by the administration device to the third unit, and reporting the precise time of administration by the third unit to the dynamic SPECT camera 10. This method may be employed for example, when administration takes place at a different location than the imaging station.
3. allowing the dynamic SPECT camera 10 to image the site of administration, for example, the arm of the patient, while administration takes place, while employing the timing mechanism 30 of the dynamic SPECT camera 10. A marker, for example, a line of radioactive ink may drawn, for example, on the patient's arm or on the administration device, for defining the time of administration as the time the radiopharmaceutical first crosses the marker. Alternatively, observing a flow of the radiopharmaceutical in the administration device or in the patient's vein may be used to determine the time of administration.
4. Observing a transparent administration device, for example, with a video camera, associated with a clock, may be employed for defining a time of administration based on the radiopharmaceutical distribution in the administration device, or based on the time the radiopharmaceutical first crosses a marker, visible by the video camera. Communication between the video camera and the dynamic SPECT camera 10, or between the video camera, the dynamic SPECT camera 10, and a third unit will provide the information to the dynamic SPECT camera 10.

In accordance with embodiments of the present invention, the administration may include various administration profiles, for example, bolus, continuous drip, or sinusoidal.

Cardiac Gating

The timing mechanism 30 of the dynamic SPECT camera 10 may further be employed for cardiac gating, which is described in detail under a corresponding section, hereinbelow.

When cardiac gating is employed, time binning to time intervals no greater than 50 milliseconds is employed.

Reference is now made to FIGS. 5C-5F, which illustrate cardiac gating in accordance with the present invention.

In essence, two different approaches are presented for cardiac gating. In the first, the cardiac RR cycle is divided to a predetermined number of graduations, for example, 16 or 32, so each is of somewhat different time span. In the second, a predetermined graduation time length is chosen, together with an alignment mark for aligning the graduations with a specific state of the RR cycle, and a discard zone is provided, generally around the U-wave region, since the RR cycle may not be exactly divisible by the predetermined graduation time lengths. The cardiac gating may be performed with respiratory gating.

Thus, in accordance with a first embodiment of the present invention, illustrated in FIG. 5C, a method of radioactive-emission imaging of a heart is provided, comprising:

imaging the heart of a body, for an imaging period greater than at least 2 cardiac electrical RR cycles 81;

post processing for identifying an average RR interval, based on actual RR time intervals 82, for the body;

post processing for evaluating each specific cardiac electrical cycle, vis a vis the average RR interval, and identifying each of the specific cardiac electrical cycles 81, either as "good," which is to be included in the imaging, or as "bad,", for example, due to Arrhythmias, wherein the "bad" cycles are discarded;

dividing each of the "good" cardiac electrical cycles to a fixed number of time graduations 83, for example, 16 or 32;

indexing each graduation 83 with cardiac-cycle indices 84, which associate each graduation with a cardiac-cycle time bin, based on its relative position in the cardiac cycle, for example, with respect to the P-wave, T-Wave, U-wave (see FIG. 5F), for example, by assigning a common bin to each P-wave peak, and another common bin to each U-wave dip, and so on; and adding up photon counts that occurred within the graduations of the same cardiac-cycle bin, from the different "good" RR cycles 81.

Additionally, the method may include performing ECG, concurrent with the imaging, and using the ECG input for identifying durations of the RR intervals 82.

In accordance with an additional embodiment, illustrated in FIG. 5D, the method includes:

extending the imaging period to cover at least two respiratory cycles 85;

dividing each of the respiratory cycles 85 to respiratory-cycle stages and assigning each of the respiratory-cycle stages a respiratory-cycle index, dividing it into bins, such as bins 86 or 87;

adding up photon counts that occurred within the graduations of common cardiac-cycle and respiratory-cycle bins, such as cardiac-cycle index 96 and respiratory index 86, or cardiac-cycle index 97 and respiratory index 87, so as to eliminate respiratory effects.

In accordance with an alternative embodiment, illustrated in FIG. 5C, the graduations 83 are fine graduations, and further including:

amalgamating the fine graduations 83 to coarse graduations 89, wherein each of the coarse graduation 89 includes at least two fine graduations 83;

indexing each coarse graduation of each of the dedicated graduation time scales with cardiac-cycle indices 91 (analogous to the cycle 84); and adding up photon counts that occurred within the coarse graduations 89 of the same cardiac-cycle index bin, for the different "good" RR cycles.

In accordance with an embodiment of the present invention, for each voxel of a reconstructed image, adding up photon counts includes adding up photon counts which occurred within the graduations of the same cardiac-cycle index, for that voxel, from the plurality of detecting units 12.

Alternatively, for each voxel of a reconstructed image, adding up photon counts includes adding up photon counts which occurred within the graduations of common cardiac-cycle and respiratory-cycle indices, for that voxel, from the plurality of detecting units 12.

Figure 5E:
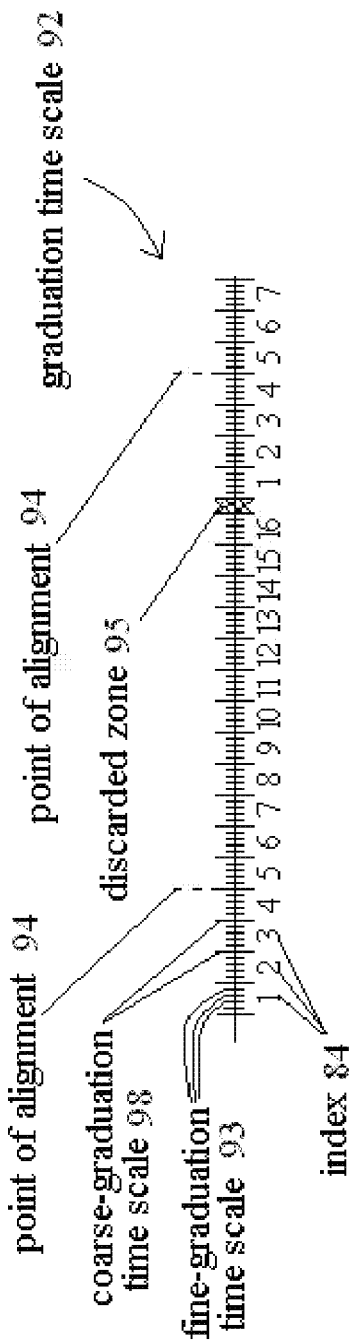
Figure 5F:
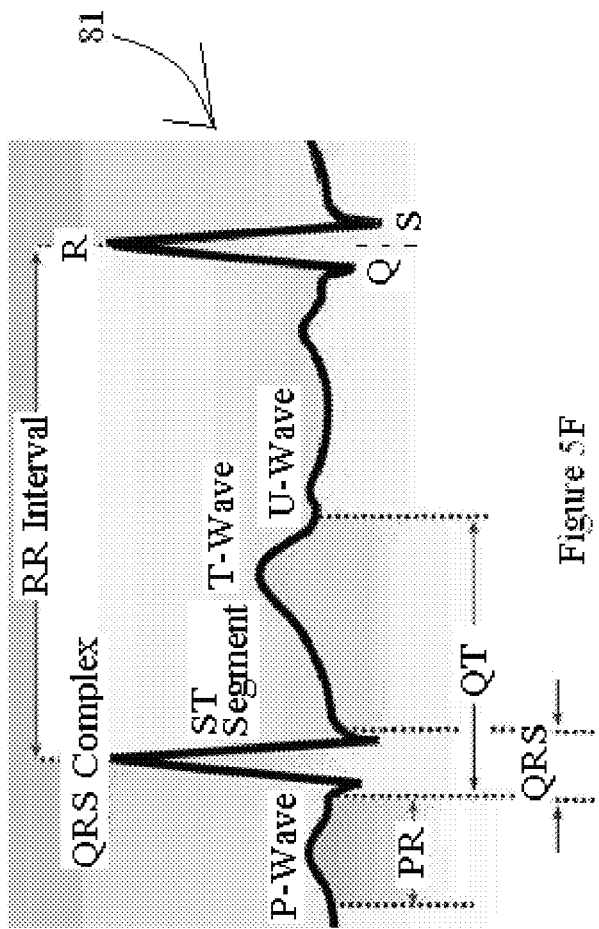

In accordance with another embodiment of the present invention, illustrated in FIG. 5E, a method of radioactive-emission imaging of a heart, comprises:

providing a fixed graduation time scale 92, with graduations 93 and at least one graduation mark 94, operative as a point of alignment;

aligning the point of alignment with a specific stage of each of the cardiac electrical cycles, such as "Q," or "R," thus, in effect assigning each one of the cardiac electrical cycles 81 a dedicated one of the graduation time scales 92; and allowing for a discard zone 95, between adjacent ones of the dedicated graduation time scales 92, where necessary.

Furthermore, the method includes using the ECG input for the aligning of the point of alignment 94 with the specific stage of each of the cardiac electrical cycles, such as "Q," or "R.

It will be appreciated that when stop and shoot acquisition mode is used, the motion of the assemblies 20 is planned to take place during specific portions of the RR cycle.

Spatial and Temporal Resolution

In order to meet the time scale considerations, described hereinabove, the dynamic SPECT camera 10 according to embodiments of the present invention is designed at least for acquiring a tomographic reconstruction image of about 15×15×15 cubic centimeters, which is approximately the volume of a heart, at a predetermined spatial resolution of at least 10×10×10 cubic millimeters, at an acquisition time no greater than about 30 seconds. Preferably, the acquisition time is no greater than about 10 seconds, and more preferably, the acquisition time is no greater than about 1 second.

Additionally, the spatial resolution of the tomographic reconstruction image may be at least 7×7×7 cubic millimeters, or better yet, at least 4×4×4 cubic millimeters, or better still, at least 1×1×1 cubic millimeters.

When cardiac gating is employed, time binning to time intervals no greater than 50 milliseconds is employed.

Dynamically Varying Time-Bin Lengths

There are times when dynamically varying time-bin lengths are desired. For example, Tc-99m-teboroxime has an uptake curve (FIG. 5B) which is very steep during the uptake and which becomes less so during the washout. Thus, different time-bin lengths may be desired for different portions of the Tc-99m-teboroxime uptake curve. Similarly, different radiopharmaceuticals have different uptake curves, and dedicated time-bin lengths may be desired for each radiopharmaceuticals, and for different portions of their respective uptake curves. Moreover, the cardiac RR cycle has very steep periods, during the rise and fall of the R peak (FIG. 5F), followed by periods that are nearly flat as a function of time. Again, time bin lengths of different durations may be employed for the different portions of the RR cycle. Furthermore, while the actual region of interest, for example, the heart, requires imaging at a very high level of accuracy, adjacent regions, for example, the chest muscle, may be of lesser interest, and may be viewed at time bins of greater lengths. Additionally, continuous acquisition mode may require shorter time-bin lengths than stop and shoot mode.

For example, the actual rise and fall of the R peak may be gated at time bins of 10 milliseconds, while the nearly leveled U-wave may be gated at 100 milliseconds. Similarly, while the heart muscle may be gated at an average time bin of 50 milliseconds, the adjacent chest muscle may be gated at time bins of 1 second and longer. It will be appreciated that other values may similarly be employed.

In accordance with embodiments of the present invention, a lookup system of recommended time-bin lengths may be provided, for specifying recommended time-bin lengths as functions of at least one of the following:

a specific region of interest;

an administered radiopharmaceutical;

time elapsed since the administration of the radiopharmaceutical;

cardiac state with respect to an RR cycle;

a view of the detecting unit 12, with respect to the region of interest;

patient general data; and data acquisition mode.

The lookup system may be, for example, tables or curves.

Thus the dynamic SPECT camera 10 may be configured for time binning at dynamically varying time-bin lengths, by providing communication between the timing mechanism 30 and the lookup system, wherein the timing mechanism is configured for selecting a recommended time-bin length from the lookup system, for each time bin.

Dynamically Varying Spectral Bins

It is sometimes of value to image only a specific spectral bin so as to eliminate scatter or contributions from other radiopharmaceuticals. Additionally, it may be of value to image several spectral bins simultaneously, for different radiopharmaceuticals, wherein different groups of detecting units are dedicated to different spectral bins.

Thus, the dynamic SPECT camera 10 may be configured for dynamically determining a spectral energy bin for each detecting unit 12, as follows:

providing a spectral selection mechanism 56 (FIG. 1A), for enabling a selection of a spectral energy bin to be used for each detecting unit 12, independently from the other detecting units 12; and a lookup system of recommended spectral energy bin values, as functions of at least one of a specific region of interest, an administered radiopharmaceutical, time since the administration of the radiopharmaceutical, a view of the detecting unit with respect to the region of interest, and patient's details;

wherein the spectral selection mechanism 56 is further configured for dynamically determining the spectral energy bin for each detecting unit, as functions of the specific region of interest, the administered radiopharmaceutical, the time elapsed since the administration of the radiopharmaceutical, the view of the detecting unit with respect to the region of interest, and patients' details, from the lookup system.

The spectral energy bin is designed to include a primary photon energy ±10%, or the primary photon energy ±7%, or the primary photon energy ±5%.

Additionally, at least two radiopharmaceuticals may be administered and viewed by different groups of detecting units, each group being configured for a different spectral energy bin, so as to view each radiopharmaceutical in the same region independently of the other radiopharmaceutical.

The spectral selection mechanism may be a hardware unit or a software.

The spectral selection may be performed during data acquisition, or later.

Intracorporeal dynamic SPECT Camera

Referring further to the drawings, FIGS. 6A-6I describe the dynamic SPECT camera 10 as an intracorporeal dynamic SPECT camera 10, which includes a single assembly 20, preferably configured for oscillatory sweeping motion around its longitudinal axis—the z axis, as described by the arrow 60. The blocks 18 may be further configured for oscillatory sweeping motion in an orthogonal direction, as described by the arrows 70. An end block 18' may be further configured for motion, for example, as described by the arrow 70'. It will be appreciated that other motions are similarly possible, for example, oscillatory lateral motions, or rotational motions. For example, the arrow 90 describes the oscillatory lateral motion along the z axis of the assembly 20.

An ultrasound transducer 45 may be included with the intracorporeal dynamic SPECT camera 10.

Other features of the intracorporeal dynamic SPECT camera 10 are as described for the dynamic SPECT camera 10 of FIGS. 1A-1D.

FIG. 6A illustrates the intracorporeal dynamic SPECT camera 10 as a single rigid unit, for example, for rectal or vaginal insertion. FIG. 6C illustrates the intracorporeal dynamic SPECT camera 10 as having an incorporeal portion 44, an extracorporeal portion 42 and a cable 46, for example, for insertion to the esophagus.

Figure 6E:
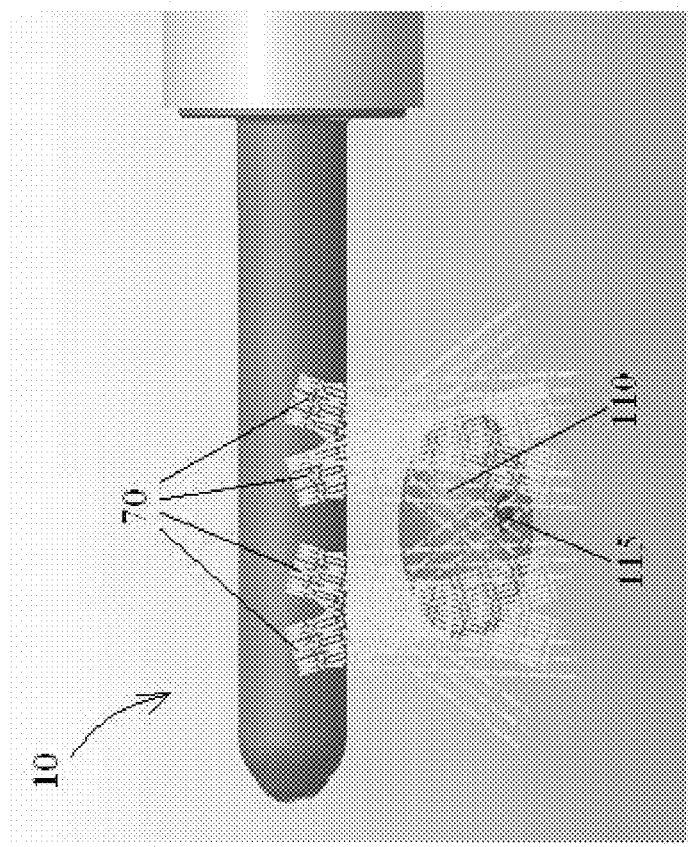
Figure 6F:
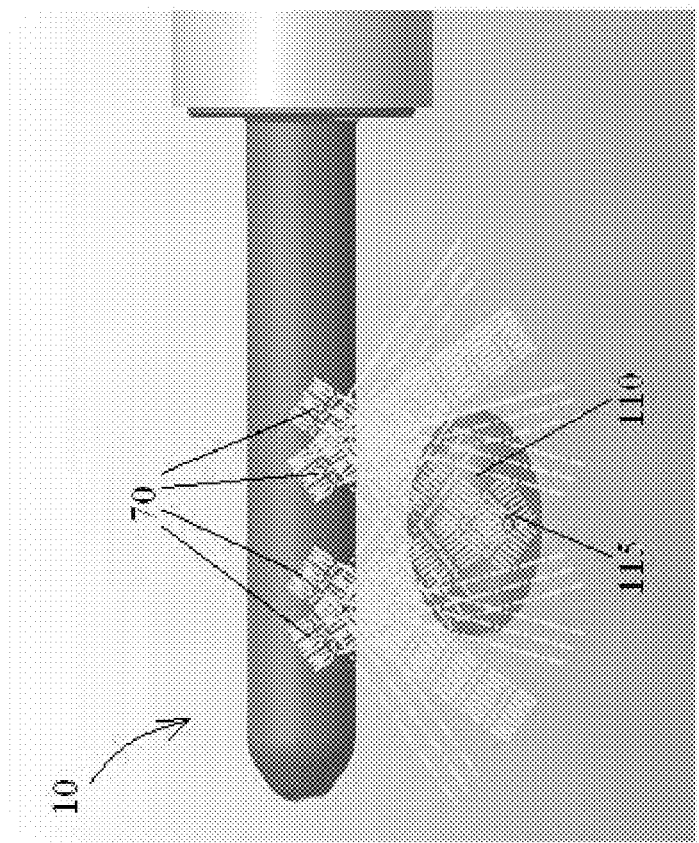
Figure 6I:
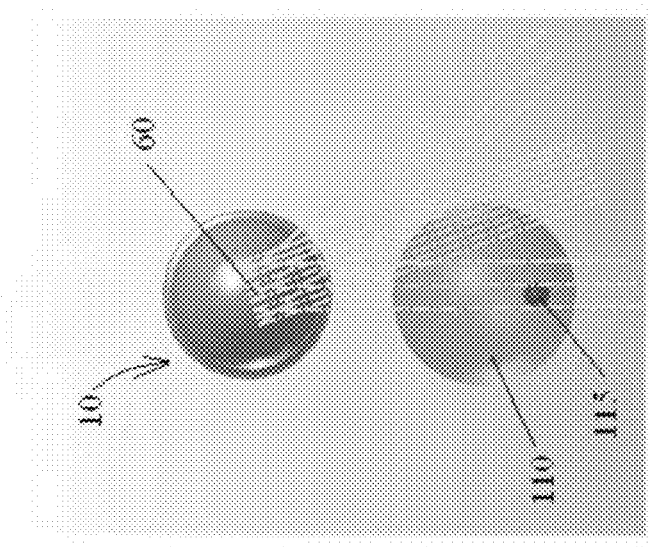
Figure 6H:
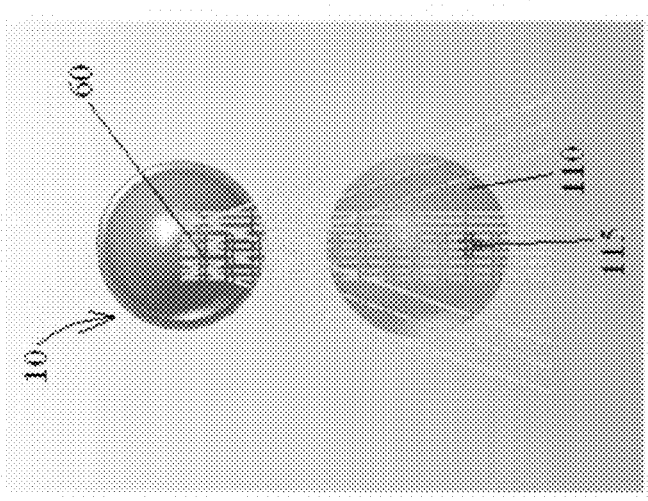
Figure 6G:
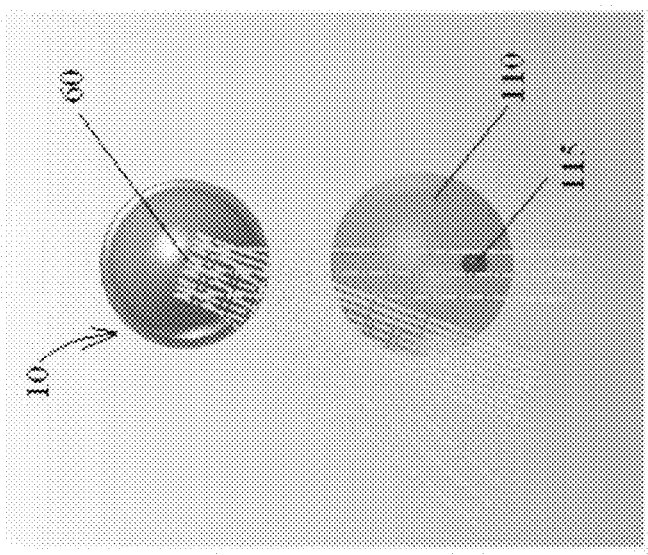

FIGS. 6F and 6E illustrate motions of the blocks 18, as described by the arrows 70. FIGS. 6F-6I illustrate motion of the assembly 20, as described by the arrow 60.

Image Acquisition Modes

In accordance with embodiments of the present invention, several image acquisition modes are available, as follows:

In a continuous acquisition mode, also referred to as fanning, data is acquired while the array, assembly, or block are in continuous motion. Continuous acquisition mode may apply also to oscillatory motions, although strictly speaking there is a momentary pause with each change of direction. This mode leads to some blurring of the data, but it does not require the array, assembly, or block to stabilize between periods of motion and periods of stationary data acquisition.

In a stop and shoot acquisition mode, incremental travels are followed by stationary acquisition intervals. This mode leads to better resolution, yet it requires a damping period, to allow the array, assembly, or block to stabilize between periods of motion and periods of stationary data acquisition, as discussed hereinbelow, under the heading, "Stability and Damping Time".

Interlacing is a fast stop and shoot acquisition mode with oscillatory motion, for example, sweeping oscillatory motion, wherein on rather than stopping at each predetermined locations, with each sweep, the odd locations are visited on a right sweep and the even locations are visited on the left sweep, or vice vera, so that each sweeping direction stops at different locations.

Prescanning relates to a fast prescan of a subject undergoing diagnosis, to identify a region-of-interest, and thereafter collect higher quality data from the region-of-interest. A prescan according to the present invention may be performed by the dynamic SPECT camera 10, preferably, with interlacing, or in a continuous mode, or by any other imaging device, including, for example, ultrasound or MRI.

Stability and Damping Time

Stop and shoot acquisition mode involves discontinuities in motion between travel and shooting modes, and at the beginning of each shooting mode, the assemblies 20 must be allowed to stabilize till vibrations are less than about ±0.25 mm, so as not to interfere with the acquisition.

Prior art SPECT cameras must allow for a damping time of about 5 seconds, but the dynamic SPECT camera 10, according to embodiments of the present invention reaches stability in about 1 second or less.

FIG. 7 schematically illustrate the assembly 20, according to embodiments of the present invention. The damping time for the assembly 20 may be described as:

$$\text{Damping Time} = CX[(1/12)M(T^2+W^2)+MX_0^2],$$

wherein:

M is the mass of the assembly 20;
T is the thickness of the assembly 20;
W is the width of the assembly 20;
$X_0$ is the axis of rotation; and
C is a constant that depends on the braking force applied to the assembly 20.

The factor 1/12 is calculated assuming the assembly proximal end is tangential to the sweeping path.

As the damping time equation illustrates, the damping time is highly dependent on both the axis of rotation $X_0$ and the mass of the assembly 20.

In the present case, the axis of rotation is that of the sweeping motion described by the arrow 60 (FIG. 1A), which is considerably shorter than an axis of rotation around the body 100.

Similarly, the mass of a single assembly is far less than that of a conventional SPECT camera.

Possible values for the assembly 20, according to embodiments of the present invention may be:

Weight of the assembly 20≈1.5 kg.
Thickness of the assembly 20≈5 cm.
Width of the assembly 20≈7 cm.

As such, the assembly is designed with a damping time constant of under 50 msec during which vibrations amplitude subsides to under 0.25 mm.

It will be appreciated that the present example applies to both extracorporeal and intracorporeal dynamic cameras.

Stationary Dynamic SPECT Camera

It may be desired to perform imaging, especially prescanning with a stationary camera, that is without motion, for the following reasons:

1. in continuous acquisition mode, the blurring produced by the motion is eliminated;

2. in stop and shoot acquisition mode, the time spent in motion is avoided, as are the vibrations, associated with the discontinuities between the motions and the stationary intervals.

In general, a stationary camera does not provide sufficient viewing positions and detecting units, yet the camera may be specifically designed to provide those, to a desired level.

Preferably, the assemblies 20 are positioned at optimal positions prior to imaging, and imaging takes place while the camera is stationary.

Thus, in accordance with embodiments of the present invention, there is provided a stationary dynamic SPECT camera 10, which is described herein with reference to FIGS. 1A-1D. The stationary dynamic SPECT camera 10 comprises:

the overall structure 15, which defines proximal and distal ends with respect to a body;

the first plurality of the assemblies 20, arranged on the overall structure 15, forming an array 25 of the assemblies 20, each assembly 20 comprising:

a second plurality of detecting units 12, each detecting unit 12 including:
a single-pixel detector 14, for detecting radioactive emissions; and
a dedicated collimator 16, attached to the single-pixel detector, at the proximal end thereof, for defining a solid collection angle $\delta$ for the detecting unit; and an assembly motion provider 40, configured for providing the assembly 20 with individual assembly motion with respect to the overall structure, prior to the acquisition of radioactive-emission data;

a position-tracker 50, configured for providing information on the position and orientation of each of the detecting units 12, with respect to the overall structure 15, during the individual motion, the stationary dynamic SPECT camera 10 being configured for acquiring a tomographic reconstruction image of a region of interest while stationary, for the whole duration of the tomographic image acquisition.

Preferably, the region of interest is about 15×15×15 cubic centimeters, and the tomographic image may be acquired during an acquisition time of 60 seconds, at a spatial resolution of at least 20×20×20 cubic millimeter.

Additionally, the tomographic image may be acquired during an acquisition time of 30 seconds, at a spatial resolution of at least 20×20×20 cubic millimeter.

Furthermore, the tomographic image may be acquired during an acquisition time of 60 seconds, at a spatial resolution of at least 10×10×10 cubic millimeter.

Additionally, the tomographic image may be acquired during an acquisition time of 30 seconds, at a spatial resolution of at least 10×10×10 cubic millimeter.

Preferably, the structure 15 conforms to the contours of the body 100, for acquisition with substantial contact or near contact with the body.

Additionally, the assemblies 20 in the array 25 are configured to provide stereo views in a plane and cross views.

Anatomic Construction of Voxels

Anatomic construction of voxels avoids the smearing effect of a rigid voxel grid construction, where different tissue types, for example, blood and muscle, appear in a same voxel. This is important especially for perfusion studies, where the perfusion of blood into the tissue is sought.

Reference is now made to FIGS. 8A and 8B, which schematically illustrate a rigid voxel grid construction and an anatomic construction of voxels, respectively, in accordance with the present invention.

FIGS. 8A and 8B illustrate a heart 200, having atria 202 and 204, chambers 206 and 208, and a muscle 218.

As seen in FIG. 8A, a rigid voxel construction 202 causes smearing of the different tissue types. However, as seen in FIG. 8B, blood and muscle tissues are anatomically divided into different voxels, allowing an accurate study of perfusion. The atria and chambers are divided into an anatomic voxel system 222, or to an anatomic voxel system 224, while the muscle is divided into a relatively coarse voxel system 226, or to a finer voxel system 228, as desired. It will be appreciated that the anatomic voxels may vary in volume. For example, since ischemia is not relevant to the atria and chambers, they may be divided into coarse voxels, while the heart muscle may be divided into fine voxels.

As further seen in FIG. 8B, the rigid voxel construction 202 may still applied to the surrounding chest muscle.

It will be appreciated that parametric equations, such as F(1) and F(2) may be created and used in the construction of the anatomic construction of the voxels.

The following describes methods for obtaining the anatomic construction of voxels.

A first method for the anatomic construction of voxels includes:

providing a structural image of a region of interest, such as a heart;

constructing an anatomic system of voxels, for the region of interest, in which voxel boundaries are aligned with boundaries of structural objects of the region of interest, based on the structural image;

performing radioactive-emission imaging of the region of interest, utilizing the anatomic system of voxels; and performing reconstruction of the radioactive-emission imaging, utilizing the anatomic system of voxels.

Preferably, the structural image is provided by a structural imager, selected from the group consisting of 2-D ultrasound, 3-D ultrasound, planner x-rays, CT x-rays, and MRI.

Additionally, the structural imager is co-registered to a radioactive-emission imaging camera which performs the radioactive-emission imaging.

Moreover, attenuation correction of the radioactive-emission imaging may be performed, based on the structural image.

Furthermore, the structural image and the radioactive-emission image, constructed with the anatomic voxels, may be displayed together.

Alternatively, the structural imager is not co-registered to a radioactive-emission imaging camera which performs the radioactive-emission imaging, and further including corrections for misregistration.

Alternatively still, the structural image is provided from a lookup system, which is preferably corrected for patient's details.

It will be appreciated that the anatomic construction of voxels may be based on fitting the boundaries of the structural objects to parametric equations and utilizing the parametric equations in the constructing of the anatomic system of voxels.

Additionally, the anatomic system of voxels includes voxels of varying volumes, depending on their anatomic position and relevance.

Furthermore, the method includes time-binning of the radioactive emissions to time periods not greater than substantially 30 seconds, or not greater than substantially 10 seconds, or not greater than substantially 1 second.

Additionally, the anatomic system of voxels includes voxels of varying volumes, depending on the relevance of their dynamic activity.

An alternative method for the anatomic construction of voxels includes, relates to the use of the radioactive emission imaging itself for the anatomic reconstruction, as follows:

providing a first system of voxels for a region of interest;

obtaining radioactive-emission data from the region of interest;

performing a first reconstruction, based on the radioactive-emission data and the first system of voxels, to obtain a first image;

correcting the first system of voxels, by aligning voxel boundaries with object boundaries, based on the first image; thus obtaining a second system of voxels;

performing a second reconstruction, based on the radioactive-emission data and the second system of voxels, thus obtaining a second image.

Alternatively, a set of radioactive emission data is obtained, possibly with a second injection, in order to concentrate the viewing on the anatomic voxels, as follows:

providing a first system of voxels for a region of interest;

obtaining a first set of radioactive-emission data from the region of interest;

performing a first reconstruction, based on the first set of the radioactive-emission data and the first system of voxels, to obtain a first image;

correcting the first system of voxels, by aligning voxel boundaries with object boundaries, based on the first image; thus obtaining a second system of voxels, which is anatomically based;

obtaining a second set of radioactive-emission data from the region of interest, based on the second system of voxels, which is anatomically based; and performing a second reconstruction, based on the second set of the radioactive-emission data and the second system of voxels, thus obtaining a second image.

Anatomic Modeling

Bull's Eye, or polar map, is a semi-automatic method for the quantification and evaluation of coronary artery disease from SPECT tomograms obtained by marking the myocardium with Tl-201 or MIBI-Tc-99. The polar map is computed from cross-sectional slices of the Left Ventricle (LV). For each slice, the center and a radius of search that contains the LV are determined and the LV is divided into radial sectors. The maximum count value of each sector is computed, generating a profile. Profiles are plotted as concentric circle onto the map. The resulting map is a compression of 3D information (LV perfusion) onto a single 2D image.

Yet the bull's eye or polar map is reconstructed from a rigorous geometry of voxels, for example, of 5×5×5 mm, or 4×4×4 mm, which cuts across tissue types, thus providing smeared information.

A voxel division that is based on an anatomical structure would be highly preferred, as it would allow the measurements of processes within and across anatomical features, substantially without the smearing effect. For example, if specific voxels are used to define blood regions, and others are used to define muscle regions, than diffusion across boundary membranes and other processes may be evaluated, substantially without a smearing effect.

Anatomical model is based on voxels that follow anatomical structures, and may be shaped for example, as a sphere, a tube, or as a shell segment, rather than as a the standard cube.

When combined with a camera of high resolution and sensitivity and with gated measurements, anatomic modeling would be clearly advantageous over standard, rigorous modeling, especially for kinetic studies are meaningful only with respect to specific tissue types.

In accordance with embodiments of the present invention, the polar map may be produced with a reduced number of amplitudes, or levels, for example, 7 levels of severity, or 5 levels of severity, from healthy to severe.

Kinetic Modeling

As part of the imaging and analysis processes, the camera may be able to produce a time series of 2D or 3D images, showing reconstructed intensity in space and its changes over time.

Likewise, it may be desirable not to reconstruct the entire volume but only limited segments of interest. In those segments, resolution of segment definition may be very important in order to minimize partial volume effect, which results in a biased estimate of the kinetic process.

In an exemplary embodiment, the analysis of the kinetic process may be after reconstruction of the intensity in the entire volume or in the selected segments has been done for a series of time points. In that case, each segment or location in space (u) has a list of intensity (I) values in time (t), and the list I(u,t) may be further analyzed to fit parametric kinetic model.

Such a parametric kinetic model may be a variety of kinds, depending on the modeling on the biological process. Examples of such models may be found in PCT/IL2005/001173.

In a simplistic example, the model may be $$I(u,t) = B(t) \cdot (1 - e^{-k_1(u) \cdot t}) \cdot e^{-k_2(u) \cdot t}$$

where B(t) is a concentration in the blood, whether obtained from imaging a segment which is pure blood (e.g. major blood vessel, or volume within the heart chamber), or may be known from other sources (by injection profile, other invasive or non invasive measurements from the blood, etc). $k_1(u)$ is the time constant representing a process of uptake into the tissue at segment u, and $k_2(u)$ is the time constant representing a process of washout from the tissue at segment u.

There may be many other models, and for example the equation above may take other forms such as $$I(u,t) = B(t) * F_1(k_1(u),\tau) * F_2(k_2(u),\tau)$$

where * stands for either multiply operation or convolution in most cases, and $F_1$ and $F_2$ represent processes. In an example, the effect of such process on the intensity may be modeled in linear cases by convolution of the intensity in the blood with an impulse response of a linear process $F_1(k_i(u),\tau)$. Each of these may include one or more time constants $k_i(u)$, and the time profile is described as a function of time $\tau$. There may be one or more such processes $F_i$, for example 1 (e.g. uptake or decay only), 2 (e.g. simultaneous uptake and clearance processes, 3 (e.g. combination with accumulation or metabolism), 4 or more.

A process of fitting may be used between the reconstructed intensity in space and time and the parametric models mentioned above.

In another example, the parametric model may be incorporated into the reconstruction process. In this case, it is not necessary to perform reconstruction of intensities I(u,t) in space and time and then use that information to extract time constants of biological processes $k_i(u)$.

Instead, the imaging equation $$y_n(t) \sim \text{Poisson}\left(\left[\sum_u \varphi_n(u) I(u,t)\right]\right)$$

may be explicitly replaced with the model of the intensities $$y_n(t) \sim \text{Poisson}\left(\left[\sum_u \varphi_n(u)B(t) * F_1(k_1(u), \tau) * F_2(k_2(u), \tau)\right]\right)$$

(where $y_n(t)$ is the number of photon measured from a viewing position n with a probability function of the view $\phi_n(u)$).

In this case, the reconstruction process (e.g. by Maximum-Likelihood, Expectation maximization, or other equation solving techniques) is used to recover the best fitting values of $k_i(u)$, instead of recovering $I(u,t)$ and then $k_i(u)$.

In some embodiments of the present invention, the use of a camera directly intended to perform dynamic studies, the ability to avoid interim recovery of intensities in 3D-space in various time periods may be a benefit, as the design of the scanning is optimized for the kinetic parameters reconstruction, and not necessarily to image quality in each time point.

Active Vision

The camera of the present invention may further include active vision which relates to a method of radioactive-emission measurements of a body structure, comprising:

performing radioactive-emission measurements of the body structure, at a predetermined set of views;

analyzing the radioactive-emission measurements; and dynamically defining further views for measurements, based on the analyzing.

Active vision may be used, for example, to better define an edge, by changing a view direction, to direct a saturating detecting unit away from a hot spot, to change the duration at a certain location, when a greater number of counts are required, or when sufficient counts have been obtained.

Reconstruction Stabilizer

The method of reconstruction employed by the present invention may further include a method for stabilizing the reconstruction of an imaged volume, comprising:

performing an analysis of the reliability of reconstruction of a radioactive-emission density distribution of said volume from radiation detected over a specified set of views; and defining modifications to at least one of a reconstruction process and a data collection process to improve said reliability of reconstruction, in accordance with said analysis.

Additionally, the method may include calculating a measure of said reliability of reconstruction, said measure of reliability of reconstruction being for determining a necessity of performing said modifications.

Furthermore, the method may include:

providing a detection probability matrix defining a respective detection probability distribution of said volume for each of said views; calculating the singular values of said detection probability matrix;

identifying singular values as destabilizing singular values.

Additionally, the method may include calculating a condition number of said probability matrix as a measure of said reliability of reconstruction.

It will be appreciated that this approach may result in non-uniform voxels, wherein voxel volume may increase or decrease as necessary to increase the reliability of the reconstruction View Selection The present invention further utilizes a method of optimal view selection, as follows:

providing said volume to be imaged;
modeling said volume;
providing a collection of views of said model;

providing a scoring function, by which any set of at least one view from said collection is scorable with a score that rates information obtained from said volume by said set;

forming sets of views and scoring them, by said scoring function; and selecting a set of views from said collection, based on said scoring function for imaging said volume.

Additionally, zooming in onto a suspected pathology may be performed by a two-step view selection, wherein once the suspected pathology is observed, that region of the volume is modeled anew and a new collection of views is obtained specifically for the suspected pathology.

Experimental Results

Reference is now made to FIGS. 9A-9J, which schematically illustrate cardiac imaging of Tc-99m-Teboroxime, with the dynamic camera 10 in accordance with aspects of the present invention. The significance of the experimental data provided herein is the ability to successfully image Teboroxime, which as FIG. 5B illustrates is washed out of the body very quickly.

Figure 9A:
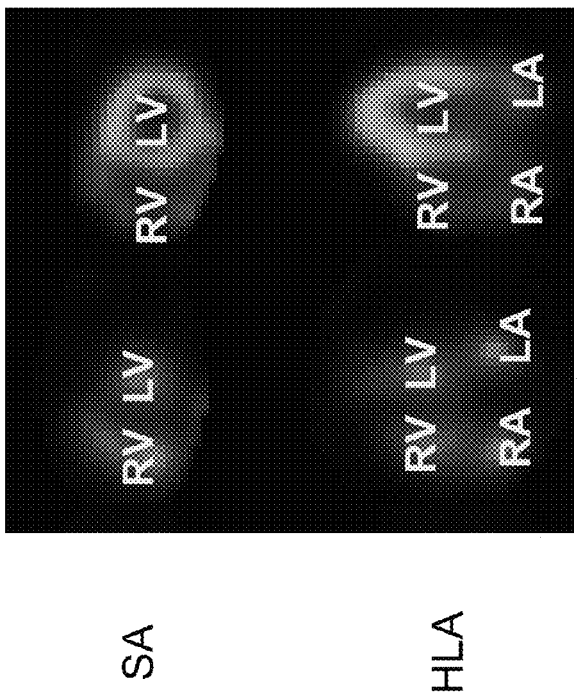

FIG. 9A provides anatomical landmarks, as follows:
Left Ventricle (LV)
Right Ventricle (RV)
Left Atrium (LA)
Right Atrium (RA)

Figure 9B:
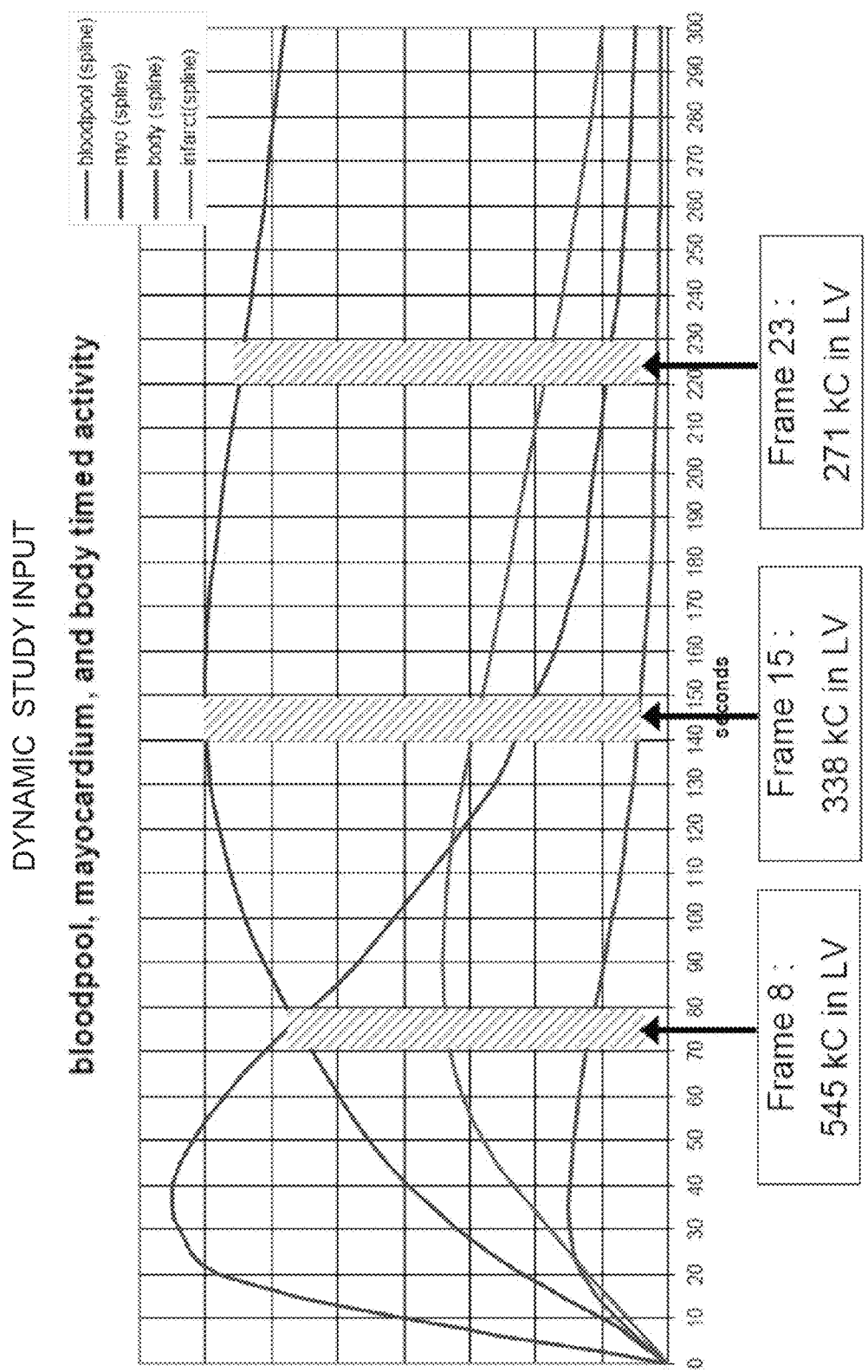

FIG. 9B is a dynamic study input of bloodpool, mayocardium, and body timed activity.

Figure 9C:
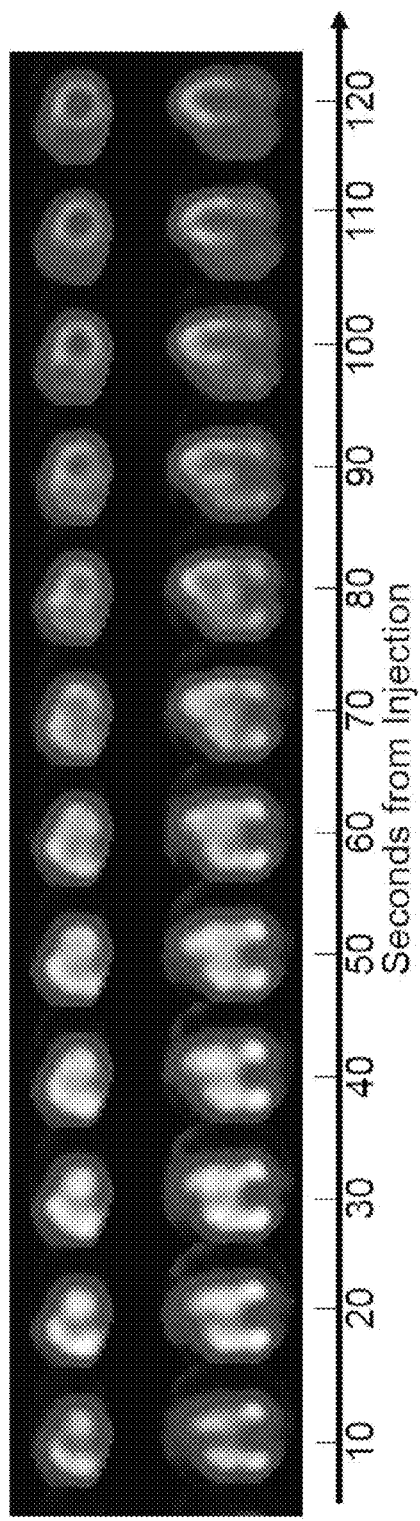

FIG. 9C is a Film-stripe representation of a dynamic SPECT study, as follows:
First 2 minutes after Tc99m-Teboroxime* injection, 10s/frame
Mid-ventricular slices (upper row:SA lower row:HLA)
Note: as the intense blood pool activity at the center of the heart chambers gradually clears, while the myocardial uptake gradually intensifies.

Figure 9D:
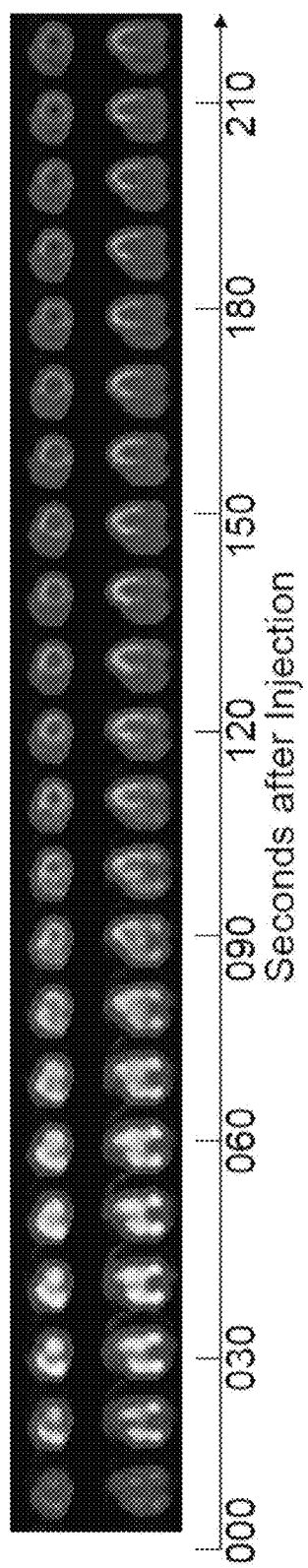
Figure 9E:
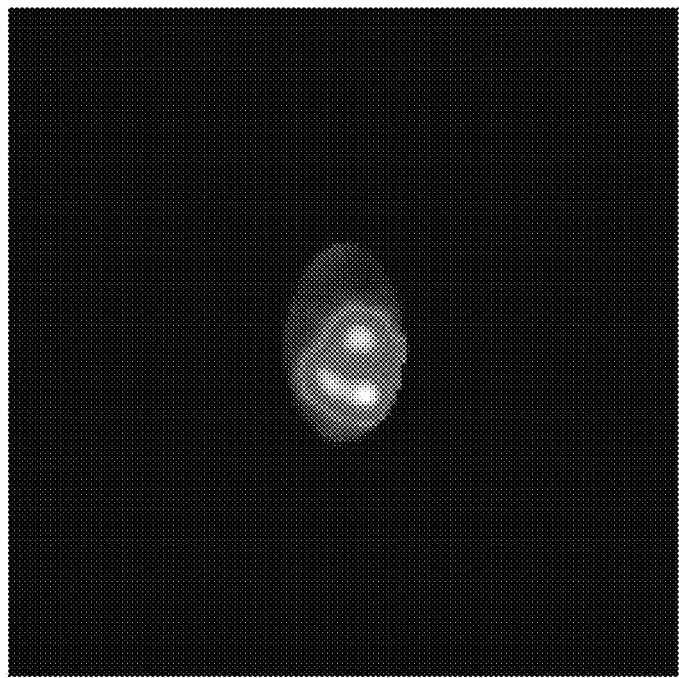

FIG. 9D is a Film-stripe representation of a dynamic SPECT study, as follows:
First 4 minutes after Tc99m-Teboroxime* injection, 10s/frame
Mid-ventricular slices (upper row:SA lower row:HLA)
Note: as the intense blood pool activity at the center of the heart chambers gradually clears, while the myocardial uptake gradually intensifies FIG. 9E is a Movie representation of a dynamic SPECT study (SA), as follows:
First 4 minutes after Tc99m-Teboroxime* injection, 10s/frame
Mid-ventricular SA slices.
Note: as the intense blood pool activity gradually clears in LV and RV cavities
Note: Myocardial uptake gradually intensifies, (the thin walled RV is less intense)

Figure 9F:
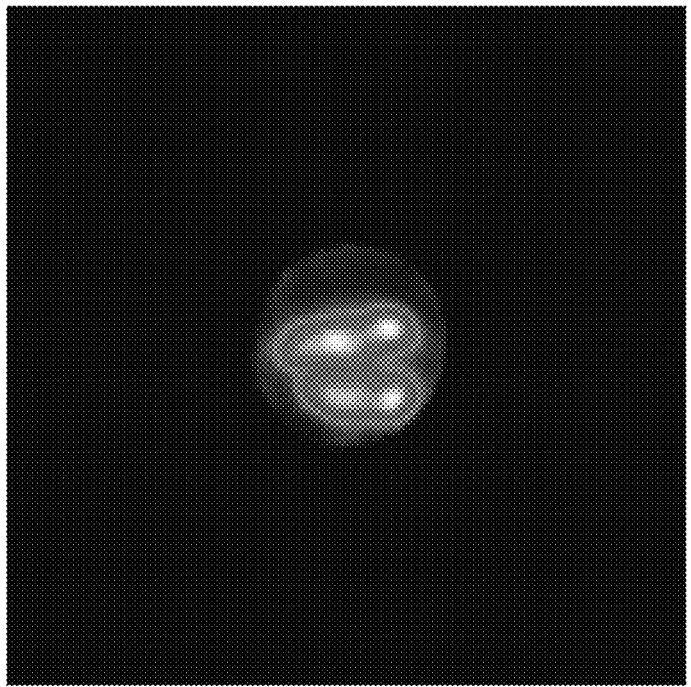

FIG. 9F is a Movie representation of a dynamic SPECT study (SA), as follows:
First 4 minutes after Tc99m-Teboroxime* injection, 10s/frame
Mid-ventricular SA slices.
Note: as the intense blood pool activity gradually clears in LV, RV, LA and RA cavities
Note: Myocardial uptake gradually intensifies, (the thin walled RV ant atria are less intense)

Figure 9G:
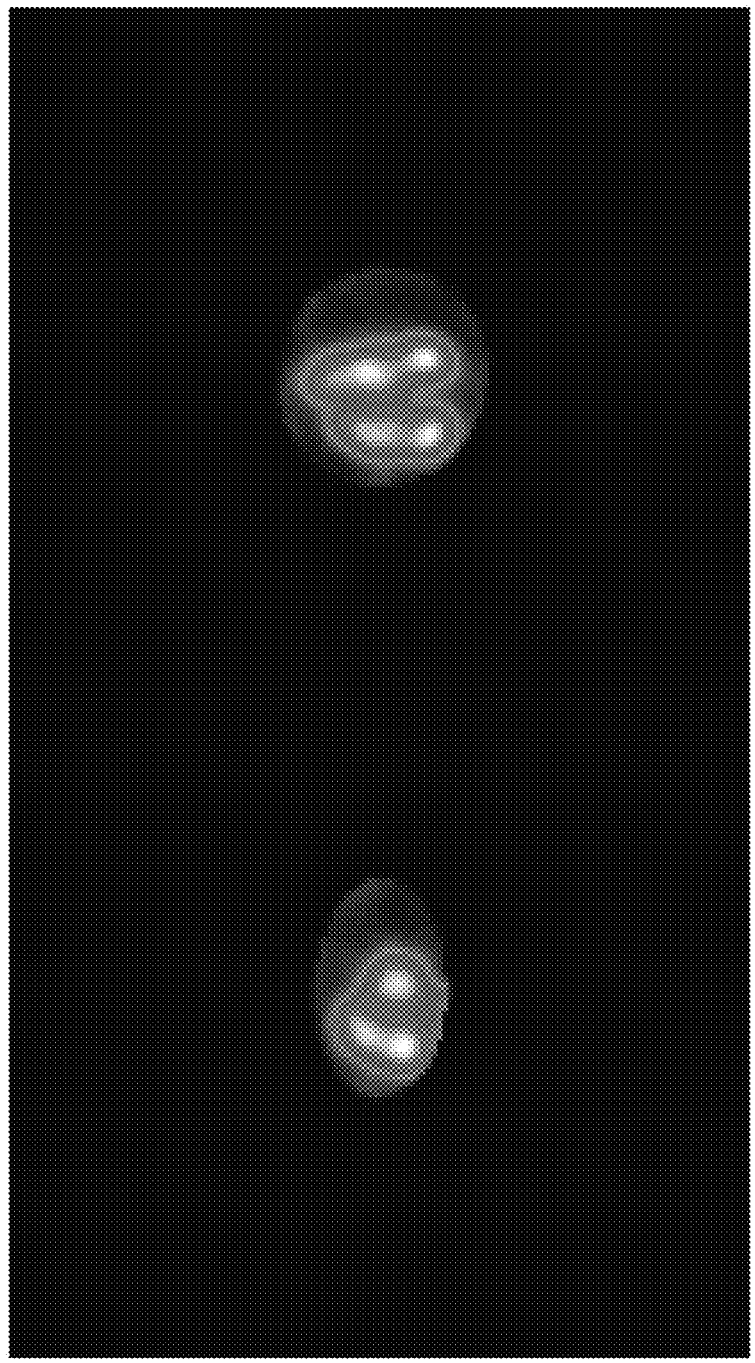

FIG. 9G is a Movie representation of a dynamic SPECT study (fast).

Figure 9H:
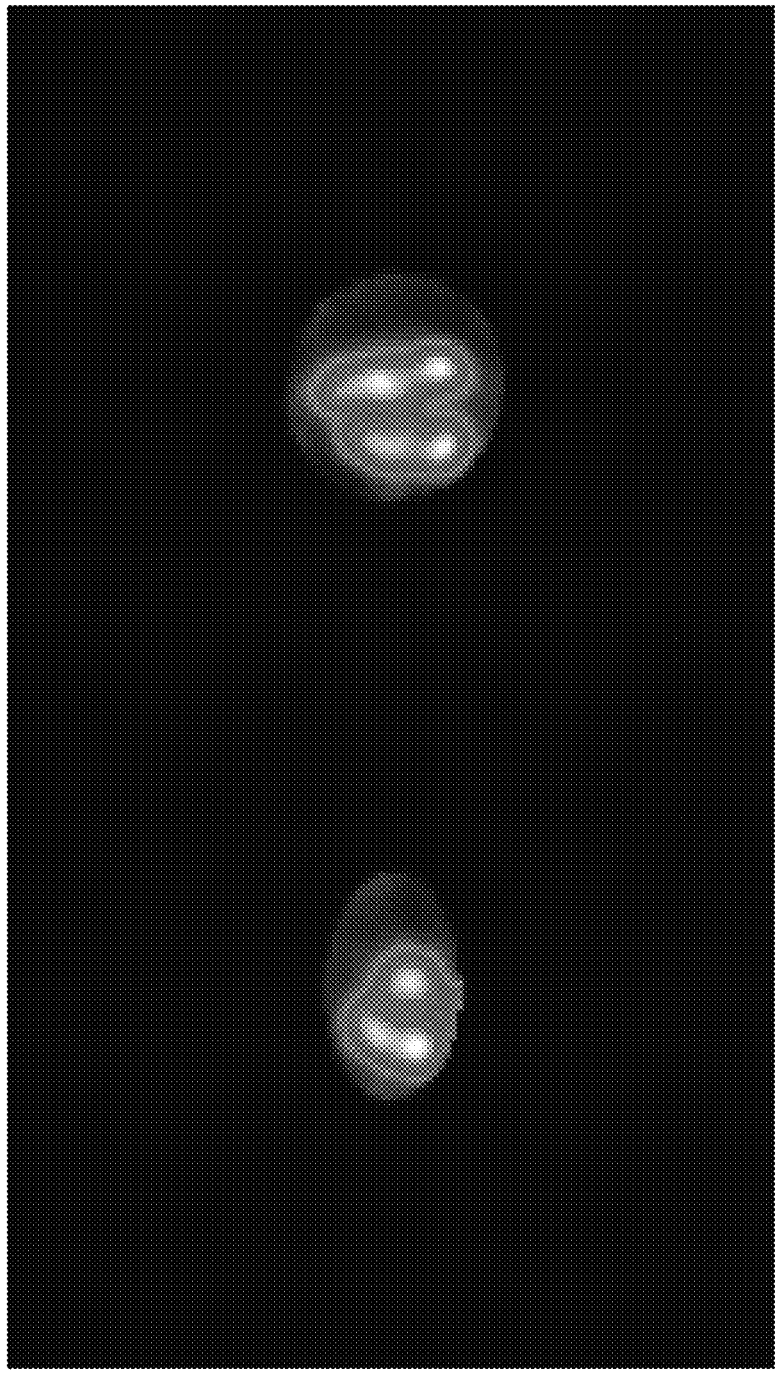

FIG. 9H is a Movie representation of a dynamic SPECT study (slow).

Figure 9I:
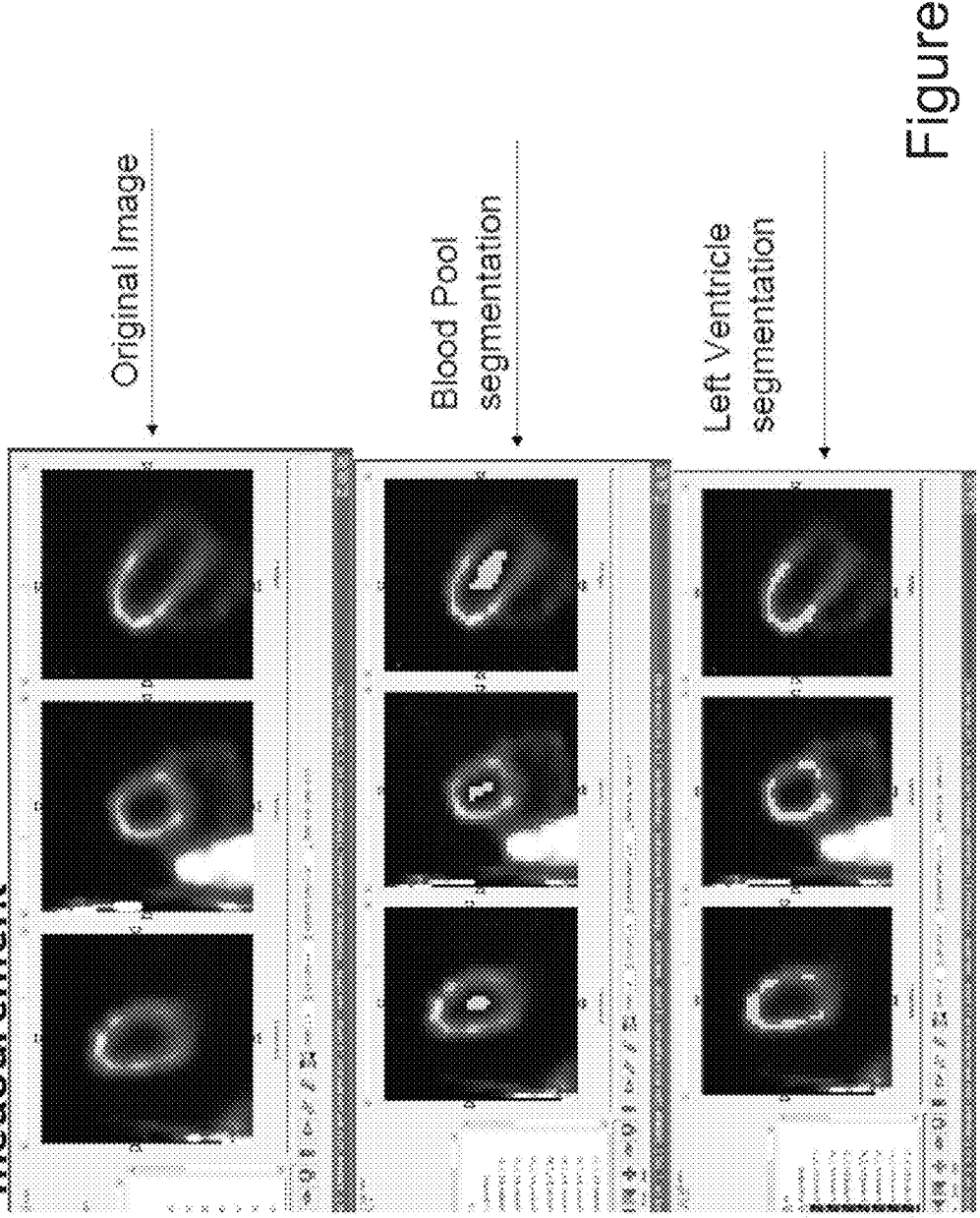
Figure 9J:
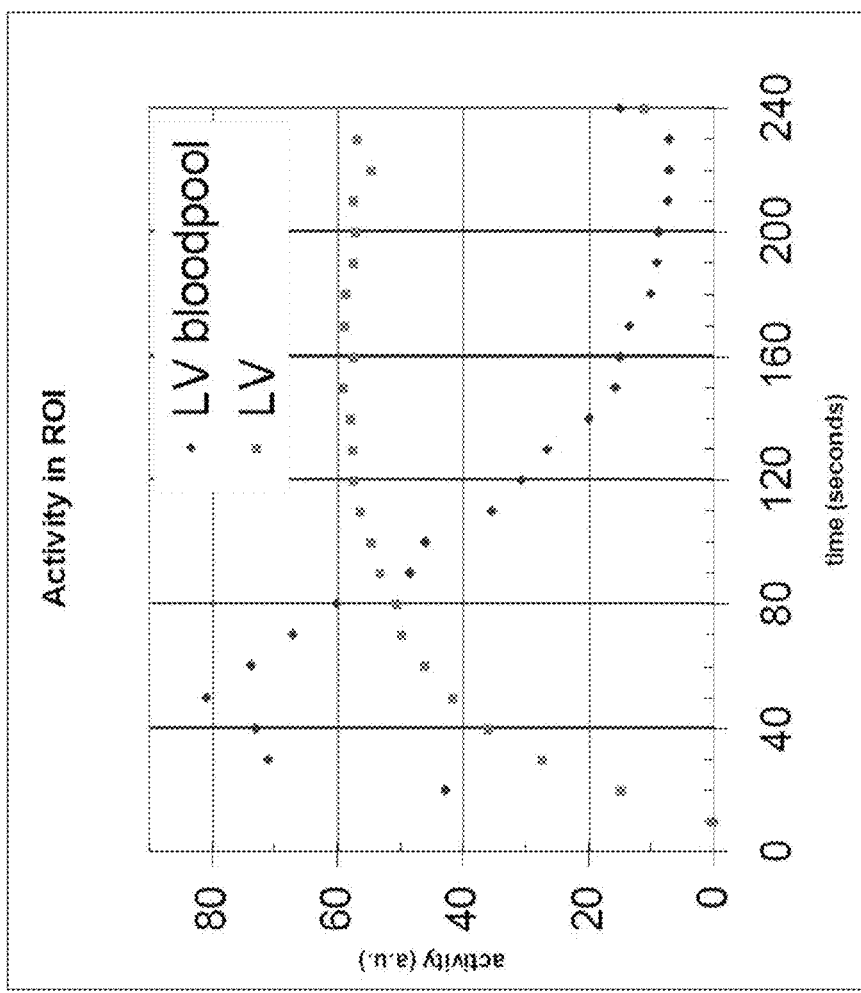

FIG. 9I represents volume segmentation for separate tissue flow dynamics measurement FIG. 9J represents measured kinetic curves.

FIG. 10 is another experiment, illustrating time binning at a rate of 0.001 seconds.

Electronic Scheme for Fast Throughput

High-sensitivity detecting units, such as the room temperature, solid-state CdZnTe (CZT) detectors utilized in the present embodiments, must be discharged frequently, as their high-sensitivity can lead to rapid saturation. When a given detector saturates, the output count for the associated pixel no longer accurately reflects the number of incoming photons, but rather the maximum number that the detector is capable of absorbing. This inaccuracy may lead to errors during reconstruction. It is therefore important to perform readout often enough to avoid detector saturation.

The data channel from the assembly 20 (or the assembly 20 readout circuitry) to the signal processing components must be fast enough to handle the large quantities of data which are obtained from the detecting units 12.

The electronic scheme of the present embodiments preferably includes one or more of the following solutions for performing frequent detector unit readout, while maintaining high data throughput to prevent data channel saturation.

In a preferred embodiment, the dynamic SPECT camera 10 includes a parallel readout unit for performing parallel readout of emission count data. Parallel readout requires less time than serial readout (in which the pixels are read out in sequence), as multiple pixels may be read out in a single cycle without losing the information of the individual pixel counts. The readout rate can thus be increased without loss of data.

Parallel readout may be performed at many levels. Reference is now made to FIG. 11, which illustrates various levels of detector unit organization at which parallel readout may be performed. The present exemplary embodiment shows a single detector array 25, which includes three assemblies 20. Each assembly includes a plurality of blocks 18 of detector units 12. Each detecting unit 12 includes a single-pixel detector (FIG. 1D).

The parallel readout unit preferably performs parallel readout at the level of one or more of:

a) detecting units 12, each of the single-pixel detector 14;
b) blocks 18, which include a plurality of detecting units 12;
c) assemblies 20, which include a plurality of blocks 18
d) array 25, which includes a plurality of assemblies 20.

When the parallel readout unit performs parallel readout at the level of the detecting units 12, count values are read out in parallel from each of the electrically insulated single-pixel detector 14. The single-pixel detector 14 is discharged at readout, and the photon collection process begins anew.

When the parallel readout unit performs parallel readout at the level of the block 18, count values from each of the detecting units 12 are read out serially, however multiple blocks 18 are read out in parallel. This approach is less complex to implement than parallel readout of the detecting units 12, although it results in a certain reduction in readout rate to accommodate the serial readout. Again, the single-pixel detectors 14 are discharged at readout.

Similarly, when the parallel readout unit performs parallel readout at the level of the assembly 20, count values from each of the detecting units 12 in the assembly 20 are read out serially, however multiple assemblies 20 are read out in parallel.

Parallel readout preferably includes multiple detection, amplification and signal processing paths for each of the pixels, thereby avoiding saturation due to a single localized high emission area—"hot spot". This is in contrast with the Anger camera, in which multiple collimators are associated with a single-pixel scintillation detector, and saturation of the scintillation detector may occur even due to a localized hot spot.

FIG. 12 illustrates an exemplary embodiment of parallel readout in the dynamic SPECT camera 10. Radioactive emissions are detected by pixelated CZT crystals, where each crystal is divided into 256 pixels. The crystal is part of a 'CZT MODULE' (B) which also includes two ASICS each receiving events from 128 pixels. The ASIC is an OMS 'XAIM3.4' made by Orbotech Medical Systems, Rehovot, Israel, together with the CZT crystal. The 2 ASICs share a common output and transmit the data to 'ADC PCB' (C) that handles four 'CZT MODULES' (B) in parallel. Thus, a total of 1024 pixels are presently channeled through one ADC board. The system is capable of further increasing the accepted event rate by channeling every two ASICS through a single ADC. The 'ADC PCB' (C) transmits the data to the 'NRG PCB' (D) that handles ten 'ADC PCB's (C) in parallel, but could be further replicated should one want to further decrease "dead time". The 'NRG PCB' (D) transmits the data to the 'PC' (E) where it is stored.

All in all, in the present embodiment, forty CZT MODULEs which contain a total of 10240 pixels transmit in parallel to the PC.

The bottle neck, and hence the only constraint, of the system data flow is the ASICS in the 'CZT MODULE' (B) and the connection to the 'ADC PCB' s (C):

1. An ASIC (128 pixels) can process one photon hit within 3.5 uSec, or 285,000 events/sec over 128 pixels, i.e. over 2200 events/px/sec-an exceedingly high rate.

2. Two ASICS share the same output, and hence coincident event output of the two ASICS in a 'CZT MODULE' (B) will cause a collision and information loss. The duration of an event output from the ASIC is 1 uSec.

When the readout is rapid, the rate at which the radiation emission data is read out of the single-pixel detectors 14 may be greater than the rate at which it may be output to the processor. One known solution for managing a difference data arrival and data processing rates is to use a buffer. The buffer provides temporary storage of the incoming data, which is retrieved at a later time.

A buffered readout configuration can result in the loss of timing information, unless active steps are taken to preserve the time information associated with the collected emission data, for example, as taught hereinabove, under the heading, "The Timing Mechanism 30."

In accordance with embodiments of the present invention, timing information is preserved. The electrical scheme may include a buffer which stores emission data along with timing information for each data item or group of data items (in the case where emission data from several detectors was obtained at substantially the same time, for example due to parallel readout), and an identification of the associated detector unit. Utilizing a buffer ensures that emission data may be collected from the detectors frequently enough to avoid saturation, even when the data channel throughput is limited. In stop and shoot mode, for example, the emission count data may be stored in the buffer for retrieval while the detector head is moving to the next location. Accurate reconstruction may thus be performed.

The camera readout circuitry is preferably designed to provide fast readout and detecting unit discharge. Fast readout circuitry may include fast analog and digital circuitry, fast A/D converters, pipelined readout, and so forth.

After the emission data has been read out of the single-pixel detectors 14, it may be necessary to convey the data to a processor for reconstruction as a single or limited number of data streams. The camera electronic scheme may include a multiplexer, for combining two or more emission data streams into a single data stream. The emission data may thus be conveyed to the processor over one physical link (or alternately over a reduced number of parallel links). For each radioactive emission event, the multiplexer includes both the timing information and an identification of the single-pixel detector 14 supplying the event. The multiplexed data may later be de-multiplexed by the processor, and reconstruction may be performed with complete information for each data item, including for example, total counts per single-pixel detector 14, per time bin, single-pixel detector location and orientation, and the time bin. Parallel readout may thus be performed, even when the collected data is to be output over a single data link.

Sensitivity Consideration

It will be appreciated that dynamic imaging with a SPECT camera has been attempted in the past, unsuccessfully, primarily, because prior-art SPECT cameras are not sensitive enough to provide tomographic reconstruction images, for example, of a heart, with sufficient object resolution, for example, 10×10×10 cubic millimeters, in less than a minute.

As a case in point, U.S. Pat. No. 7,026,623, to Oaknin, et al., filed on Jan. 7, 2004, issued on Apr. 11, 2006, and entitled, "Efficient single photon emission imaging," describes a method of diagnostic imaging in a shortened acquisition time for obtaining a reconstructed diagnostic image of a portion of a body of a human patient who was administered with dosage of radiopharmaceutical substance radiating gamma rays, using an Anger Camera and SPECT imaging. The method includes effective acquisition times from less than 14 minutes to less than 8 minutes. Oaknin, et al., do not claim an effective acquisition time of less than 7 minutes. Yet, in view of the section entitled, "Time Scale Considerations," hereinabove, a sampling rate of 8 about minutes is far too slow for myocardial perfusion studies, where a sampling rate of at least two tomographic reconstruction images per heartbeat, that is, about every 30 seconds, is desired, and furthermore, where processes occur at rates of several seconds, and must be sampled at rates of a second or less, as seen in FIG. 5B.

The dynamic SPECT camera 10 in accordance with embodiments of the present invention achieves sensitivity sufficient for the required sampling rates of between every 30 seconds and every half a second, by combining several features, specifically intended to increase sensitivity, as follows:

a collimator 16 with a solid collection angle δ of at least 0.005 steradians or greater, for a fast collection rate, and high sensitivity, wherein the loss in resolution is compensated by one or a combination of the following factors:

i. motion in a stop and shoot acquisition mode, at very small incremental steps, of between about 0.01 degrees and about 0.75 degrees.

ii. simultaneous acquisition by the assemblies 20, each scanning the same region of interest from a different viewing position, thus achieving both shorter acquisition time and better edge definitions.

iii. the structure 15 conforming to the body contours, for acquisition with substantial contact or near contact with the body.

Definition of a Clinically-Valuable Image

In consequence, the dynamic SPECT camera 10 is capable of producing a "clinically-valuable image" of an intra-body region of interest (ROI) containing a radiopharmaceutical, while fulfilling one or more of the following criteria:

1. the dynamic SPECT camera 10 is capable of acquiring at least one of 5000 photons emitted from the ROI during the image acquisition procedure, such as at least one of 4000, 3000, 2500, 2000, 1500, 1200, 1000, 800, 600, 400, 200, 100, or 50 photons emitted from the ROI. In one particular embodiment, the camera is capable of acquiring at least one of 2000 photons emitted from the ROI during the image acquisition procedure;

2. the dynamic SPECT camera 10 is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI having a volume of no more than 500 cc, such as a volume of no more than 500 cc, 400 cc, 300 cc, 200 cc, 150 cc, 100 cc, or 50 cc. In one particular embodiment, the camera is capable of acquiring at least 1,000,000 photons emitted from a volume of the ROI having a volume of no more than 200 cc;

3. the dynamic SPECT camera 10 is capable of acquiring an image of a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the radiopharmaceutical as distributed within the ROI has a range of emission-intensities I (which is measured as emitted photons/unit time/volume), and wherein at least 50% of the voxels of the reconstructed three-dimensional emission-intensity image of the ROI have inaccuracies of less than 30% of range I, such as less than 25%, 20%, 15%, 10%, 5%, 2%, 1%, or 0.5% of range I. For example, the radiopharmaceutical may emit over a range from 0 photons/second/cc to $10^5$ photons/second/cc, such that the range I is $10^5$ photons/second/cc, and at least 50% of the voxels of the reconstructed three-dimensional intensity image of the ROI have inaccuracies of less than 15% of range I, i.e., less than $1.5 \times 10^4$ photons/second/cc. For some applications, the study produce a parametric image related to a physiological process occurring in each voxel. In one particular embodiment, the image has a resolution of at least 5×5×5 mm, and at least 50% of the voxels have inaccuracies of less than 15% of range I;

4. the dynamic SPECT camera 10 is capable of acquiring an image, which has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the radiopharmaceutical as distributed within the ROI has a range of emission-intensities I (which is measured as emitted photons/unit time/volume), and wherein at least 50% of the voxels of the reconstructed three-dimensional emission-intensity image of the ROI have inaccuracies of less than 30% of range I, such as less than 25%, 20%, 15%, 10%, 5%, 2%, 1%, or 0.5% of range I. For example, the radiopharmaceutical may emit over a range from 0 photons/second/cc to $10^5$ photons/second/cc, such that the range I is $10^5$ photons/second/cc, and at least 50% of the voxels of the reconstructed three-dimensional intensity image of the ROI have inaccuracies of less than 15% of range I, i.e., less than $1.5 \times 10^4$ photons/second/cc. For some applications, the study produces a parametric image related to a physiological process occurring in each voxel. In one particular embodiment, the image has a resolution of at least 5×5×5 mm, and at least 50% of the voxels have inaccuracies of less than 15% of range I;

5. the dynamic SPECT camera 10 is capable of acquiring an image, which has a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values I, and wherein at least 50% of the voxels of the reconstructed parametric three-dimensional image have inaccuracies less than 100% of range I, such as less than 70%, 50%, 40%, 30%, 25%, 20%, 15%, 10%, 5%, 2%, 1%, or 0.5% of range I. For example, the physiological process may include blood flow, the values of the parameters of the physiological process may have a range from 0 to 100 cc/minute, such that the range I is 100 cc/minute, and at least 50% of the voxels of the reconstructed parametric three-dimensional image have inaccuracies less than 25% of range I, i.e., less than 25 cc/minute. In one particular embodiment, the image has a resolution of at least 5×5×5 mm, and at least 50% of the voxels have inaccuracies of less than 25% of range I; and/or 6. the dynamic SPECT camera 10 is capable of acquiring an image, which has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein if the radiopharmaceutical is distributed substantially uniformly within a portion of the ROI with an emission-intensity I+/−10% (which is defined as emitted photons/unit time/volume), and wherein at least 85% of the voxels of the reconstructed three-dimensional emission-intensity image of the portion of the ROI have inaccuracies of less than 30% of intensity I, such as less than 15%, 10%, 5%, 2%, 1%, 0.5%, 20%, or 25% of intensity I. For example, the radiopharmaceutical may be distributed within a volume with a uniform emission-intensity I of $10^5$ photons/second/cc, and at least 85% of the voxels of the reconstructed three-dimensional intensity image of the volume have inaccuracies of less than 15% of intensity I, i.e., less than $1.5×10^4$ photons/second/cc. For some applications, the same definition may apply to a study which produces a parametric image related to a physiological process occurring in each voxel. In one particular embodiment, the image has a resolution of at least 5×5×5 mm, and at least 50% of the voxels have inaccuracies of less than 15% of intensity I.

It is expected that during the life of this patent many relevant dynamic SPECT cameras will be developed and the scope of the term dynamic SPECT camera is intended to include all such new technologies a priori.

As used herein the term "substantially" refers to ±10%.

As used herein the term "about" refers to ±30%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for anatomic construction of voxels, comprising:
   providing a structural image of a region of interest;
   constructing an anatomic system of voxels, for the region of interest, in which voxel boundaries are aligned with boundaries of structural objects of the region of interest, based on the structural image;
   performing radioactive-emission imaging of the region of interest, utilizing the anatomic system of voxels;
   performing reconstruction of the radioactive-emission imaging, utilizing the anatomic system of voxels; and
   fitting the boundaries of the structural objects to parametric equations and utilizing the parametric equations in the constructing of the anatomic system of voxels.

2. The method of claim 1, wherein the structural image is provided by a structural imager, selected from the group consisting of 2-D ultrasound, 3-D ultrasound, planner x-rays, CT x-rays, and MRI.

3. The method of claim 2, wherein the structural imager is co-registered to a radioactive-emission imaging camera which performs the radioactive-emission imaging.

4. The method of claim 3, and further including attenuation correction of the radioactive-emission imaging based on the structural image.

5. The method of claim 3, and further including displaying the structural image and the reconstruction of the radioactive-emission imaging together.

6. The method of claim 2, wherein the structural imager is not co-registered to a radioactive-emission imaging camera which performs the radioactive-emission imaging, and further including corrections for misregistration.

7. The method of claim 1, wherein the structural image is provided from a lookup system.

8. The method of claim 7, wherein the lookup system is corrected for patient's details.

9. A method for anatomic construction of voxels, comprising:
   providing a structural image of a region of interest;
   constructing an anatomic system of voxels, for the region of interest, in which voxel boundaries are aligned with boundaries of structural objects of the region of interest, based on the structural image;
   performing radioactive-emission imaging of the region of interest, utilizing the anatomic system of voxels; and
   performing reconstruction of the radioactive-emission imaging, utilizing the anatomic system of voxels;
   wherein the anatomic system of voxels includes voxels of varying volumes, depending on their anatomic position and relevance.

10. A method for anatomic construction of voxels, comprising:
   providing a structural image of a region of interest;
   constructing an anatomic system of voxels, for the region of interest, in which voxel boundaries are aligned with boundaries of structural objects of the region of interest, based on the structural image;
   performing radioactive-emission imaging of the region of interest, utilizing the anatomic system of voxels;
   performing reconstruction of the radioactive-emission imaging, utilizing the anatomic system of voxels; and
   time-binning of the radioactive emissions to time periods not greater than substantially 30 seconds.

11. A method for anatomic construction of voxels, comprising:
- providing a structural image of a region of interest;
- constructing an anatomic system of voxels, for the region of interest, in which voxel boundaries are aligned with boundaries of structural objects of the region of interest, based on the structural image;
- performing radioactive-emission imaging of the region of interest, utilizing the anatomic system of voxels; and
- performing reconstruction of the radioactive-emission imaging, utilizing the anatomic system of voxels;
- wherein the anatomic system of voxels includes voxels of varying volumes, depending on the relevance of their dynamic activity.

12. A method of reconstruction of a radioactive emission image, comprising:
- providing a first system of voxels for a region of interest;
- obtaining radioactive-emission data from the region of interest;
- performing a first reconstruction, based on the radioactive-emission data and the first system of voxels, to obtain a first image;
- correcting the first system of voxels, by aligning voxel boundaries with object boundaries, based on the first image; thus obtaining a second system of voxels;
- performing a second reconstruction, based on the radioactive-emission data and the second system of voxels, thus obtaining a second image.

13. A dynamic SPECT camera configured for dynamically determining a spectral energy bin for each detecting unit, the camera comprising:
- an overall structure, which defines proximal and distal ends with respect to a body;
- a plurality of detecting unit; arranged on the overall structure and configured for detecting radioactive emissions in a spectral range between 10 KeV and 1 MeV;
- a spectral selection mechanism, for enabling a selection of a spectral energy bin to be used for each detecting unit, independently from the other detecting units; and
- a lookup system of recommended spectral energy bin values, as functions of at least one of a specific region of interest, an administered radiopharmaceutical, time since the administration of the radiopharmaceutical, a view of the detecting unit with respect to the region of interest, and patient's details;
- wherein the spectral selection mechanism is further configured for dynamically determining the spectral energy bin for each detecting unit, as functions of at least one of the specific region of interest, the administered radiopharmaceutical, the time elapsed since the administration of the radiopharmaceutical, the view of the detecting unit with respect to the region of interest, and patients' details, from the lookup system.

14. The dynamic SPECT camera of claim 13, wherein the spectral energy bin is designed to include a primary photon energy ±10%.

15. The dynamic SPECT camera of claim 13, wherein the spectral energy bin is designed to include a primary photon energy ±7%.

16. The dynamic SPECT camera of claim 13, wherein the spectral energy bin is designed to include a primary photon energy ±5%.

17. The dynamic SPECT camera of claim 13, and further including administering at least two radiopharmaceuticals and viewing a same region with different groups of detecting units, each group being configured for a different spectral energy bin, so as to view each radiopharmaceutical in the same region independently of the other.

18. The dynamic SPECT camera of claim 13, wherein the spectral selection mechanism is a hardware unit.

19. The dynamic SPECT camera of claim 13, and further including:
- a first plurality of assemblies, arranged on the overall structure, forming an array of assemblies, each assembly comprising:
- a second plurality of the detecting units, each of the detecting units including:
  - a single-pixel detector, for detecting radioactive emissions; and
  - a dedicated collimator, attached to the single-pixel detector, at the proximal end thereof, for defining a solid collection angle δ for the detecting unit; and
- an assembly motion provider, configured for providing the assembly with individual assembly motion with respect to the overall structure, during the acquisition of radioactive-emission data for a tomographic image.

* * * * *